United States Patent
Abe et al.

(10) Patent No.: US 7,803,605 B2
(45) Date of Patent: Sep. 28, 2010

(54) BREEDING METHOD FOR YEAST, YEAST AND A PRODUCTION METHOD FOR GLYCOPROTEIN OR BETA-GLUCAN

(75) Inventors: Hiroko Abe, Takamatsu (JP); Kenichi Nakayama, Takamatsu (JP); Yoshifumi Jigami, Tsukuba (JP); Yasunori Chiba, Tsukuba (JP); Yuki Takaoka, Takamatsu (JP); Akiko Itadani, Tokyo (JP)

(73) Assignees: National Institute of Advanced Industrial Science and Technology, Chiyoda-ku, Tokyo (JP); Neo-Morgan Laboratory Incorporated, Chiyoda-ku, Tokyo (JP)

( * ) Notice: Subject to any disclaimer, the term of this patent is extended or adjusted under 35 U.S.C. 154(b) by 335 days.

(21) Appl. No.: 11/713,540

(22) Filed: Mar. 2, 2007

(65) Prior Publication Data

US 2008/0038778 A1 Feb. 14, 2008

(30) Foreign Application Priority Data

| Jul. 14, 2006 | (JP) | ............................. 2006-193445 |
| Feb. 12, 2007 | (JP) | ............................. 2007-031396 |
| Feb. 25, 2007 | (JP) | ............................. 2007-044796 |

(51) Int. Cl.
*C12N 1/00* (2006.01)
*C12N 15/63* (2006.01)

(52) U.S. Cl. .............. 435/255.1; 435/254.1; 435/254.2; 435/254.21

(58) Field of Classification Search ....................... None
See application file for complete search history.

(56) References Cited

U.S. PATENT DOCUMENTS

2007/0077560 A1* 4/2007 Furusawa ....................... 435/6

OTHER PUBLICATIONS

Iino et al. The *Schizosaccharomyces pombe* cdc6 gene encodes the catalytic subunit of DNA polymerase delta. Mol Gen Genet. Mar. 18, 1997;254(1):93-7.*

* cited by examiner

*Primary Examiner*—Michele K Joike
(74) *Attorney, Agent, or Firm*—Osha • Liang LLP

(57) ABSTRACT

A method for breeding yeast having thermotolerance or recovering growth activity and a method for breeding yeast which produces beta-glucan efficiently as well as an yeast obtained by such methods for breeding are presented by a method for breeding yeast having thermotolerance or recovering growth activity including a step for controlling proofreading function of DNA polymerase in a loss-of-function mutant of yeast (for example, a step for including mutant pol3 gene or mutant cdc6– gene in a gene-disruptant.

3 Claims, 8 Drawing Sheets

Column Analysis of Sugar Chain Structures

BREEDING METHOD FOR YEAST, YEAST AND A PRODUCTION METHOD FOR GLYCOPROTEIN OR BETA-GLUCAN

FIELD OF THE ART

The present invention relates to a method for breeding yeast avoiding high temperature sensitivity or recovering growth activity, by inducing desirable mutations, by means of controlling proofreading function of DNA polymerase in a loss-of-function mutant of yeast such as a gene-disruptant of yeast, and the yeast obtained using such a breeding method. In more detail, the present invention relates to a method for breeding yeast whose high temperature sensitivity is avoided or whose growth activity is recovered, and yeast capable of foreign gene expression, using a loss-of-function mutant of yeast such as a budding yeast or a fission yeast producing glycoprotein with a mammalian type sugar chain by modifying amino acid sequence of DNA polymerase and inducing mutations.

Also, the present invention relates to a method for breeding yeast which produces polysaccharide (especially beta-glucan) efficiently, by inducing desirable mutations, by means of controlling proofreading function of DNA polymerase in a loss-of-function mutant of yeast such as a gene-disruptant of yeast, and the yeast obtained using such a breeding method. In more detail, the present invention relates to a method for breeding yeast whose cell wall efficiently contains beta-glucan that is used as an active ingredient in functional foods and medicine, using a loss-of-function mutant of yeast producing glycoprotein with a mammalian type sugar chain by modifying amino acid sequence of DNA polymerase and inducing mutations.

BACKGROUND ART

Many glycoproteins having sugar chains have an important function in living organisms. In addition, it is elucidated that removing a sugar chain from glycoprotein leads to disappearance of biological activity about erythropoietin (EPO) and tissue plasminogen activator (TPA) etc. (Yo Kibata, "Protein Nucleic Acids Enzyme" Vol. 36, p 775 (1991); Makoto Takeuchi "Biochemistry" Vol. 62, p 1272 (1990)). This shows that a sugar chain in glycoprotein plays an important role in biological activity. Therefore, producing glycoprotein efficiently is preferable in developing medicines.

In the case of producing glycoprotein, using yeast is considered from a viewpoint of applying techniques of genetics and molecular biology, or from a viewpoint of being a single eukaryote which has high productivity of foreign protein. On the other hand, a sugar chain produced by yeast, having many mannose added structure, shows high antigenicity in a body of higher animals. For this reason, there is a problem that glycoprotein produced by yeast might not be adequate for drugs especially being administrated through blood vessels. To resolve this problem, an yeast strain which produces a sugar chain without antigenicity was established by gene-disruption (for example, see Japanese publication of patent application 1994-277086 bulletin, Japanese publication of patent application 1995-299509 bulletin and Japanese publication of patent application 2001-161376 bulletin.)

Especially triple disruptant comprising och1 disruption (Δoch1), mnn1 disruption (Δmnn1) and mnn4 disruption (Δmnn4) is disclosed in international publication WO01/014522 pamphlet (see below patent literature 1). The document discloses the yeast any of the following gene, which relates to production of an outer sugar chain and yeast specific, is destroyed or any mutation is introduced to the following genes: alpha-1, 6 mannosyl transferase conducting first elongation reaction (OCH1); a gene coding for alpha-1, 3 mannosyl transferase which adds mannose to nonreducing end of sugar chain (MNN1); and a gene regulating addition of mannose-1-phosphate (MNN4). The yeast strain is thought to be useful for developing functional food and drugs because it is excellent in production of glycoprotein with mammalian type sugar chain.

However, the gene-disruptant shows higher temperature sensitivity than a wild strain and lower growth activity, for example, it doesn't grow at 37 degrees C. As a result, compared to wild strains, a gene-disruptant shows defective growth and has a problem that protein productivity is low.

Beta-glucan, which is a kind of polysaccharide, is known to have effects of activating macrophages, NK cells, T cells and killer T cells that attack infected cells and cancer cells in the body, and increasing immunity and resistance. With this immunity increasing effect, ability to exclude bacteria and foreign substances having entered the body is increased, so that resistance for inhibiting development of disease even if infected can be obtained. Also, with such an increase in immunity, effects of reducing allergic reactions and suppressing tumor such as cancer can be expected and antitumor effect has been actually revealed by various clinical tests. Moreover, effects such as a decrease in blood glucose level, diuretic effect, blood pressure adjustment, decrease in blood cholesterol and neutral fat levels can also be obtained.

Yeasts (especially baker's yeast) have long been used for fermented food and are extremely safe as food products. The baker's yeast, usually including about 45% of beta-glucan in the cell wall, is commercialized as a dietary supplement with a target narrowed down to immunity increasing effect. The beta-glucan of the baker's yeast is utilized by being extracted mainly from the cell wall. The beta-glucan derived from the baker's yeast is sold in the United States mainly as zymosan.

In order to obtain more beta-glucan from the cell wall of yeast, culturing yeast in large scale is required. Also, while a high-efficient extraction of beta-glucan is required after the culture, this operation is not easy since a specific technique is required. Therefore, development of a method capable of producing beta-glucan derived from yeast more easily and inexpensively by skipping such processes as much as possible is desired.

On the other hand, a mutagenesis method inducing mutation by making more than two kinds of DNA polymerase with different fidelity coexist in single *Escherichia coli* cell is known.

Moreover, in the international publication WO00/028015 pamphlet (following patent literature 2), "A method of mutation induction to a gene characterized by introducing more point mutation into one strand than the other strand of double stranded genome DNA of a cell or a living organism" (claim 1 of the bulletin) is disclosed. In the bulletin, "Mutants can be obtained effectively by accumulating more random point mutations into one DNA strand than the other strand and by reducing risks for extinction of mutagenized cells of living organisms while increasing mutation rate" is described (3rd line from the bottom of page 9 onward in the bulletin). However, while an example using *Escherichia coli* is found in the bulletin, an example using yeast is not found. Therefore, it is not quite clear about what kind of mutation is induced in the case of applying the technique disclosed in the bulletin to yeast.

(Patent literature 1) International publication WO01/014522 pamphlet (Patent literature 2) International publication WO00/028015 pamphlet

DISCLOSURE OF THE INVENTION

Problem to be Solved by the Invention

As described above, since negative traits in growth and development, such as high temperature sensitivity and reduction in growth activity are often recognized in a so-called loss-of-function mutant of yeast such as a gene-disruptant of yeast or a gene-mutant of yeast, it is an object of the present invention to provide a method for breeding yeast avoiding high temperature sensitivity or recovering growth activity, and yeast obtained by such a breeding method.

It is an object of the present invention to provide a method for breeding yeast avoiding high temperature sensitivity, or recovering growth activity, having excellent thermotolerance and productivity of protein in a loss-of-function mutant of yeast such as a gene-disruptant of yeast or a gene-mutant of yeast having ability to produce glycoprotein with a mammalian type sugar chain.

It is an object of the present invention to provide a method for producing glycoprotein with a mammalian type sugar chain using a method for breeding yeast avoiding high temperature sensitivity or recovering growth activity as mentioned above.

Also, since development of a method capable of producing beta-glucan derived from yeast more easily and inexpensively is desired, it is an object of the present invention to provide a method for breeding yeast which produces beta-glucan efficiently and yeast obtained by such a breeding method.

It is an object of the present invention to provide a method for producing beta-glucan using a method for breeding yeast which produces beta-glucan efficiently as mentioned above.

It is an object of the present invention to provide a method for breeding yeast capable of foreign gene expression, and a method for producing a foreign protein by using such a breeding method.

Means for Solving Problems

The present invention is basically based on experimental evidences having succeeded in breeding novel mutants of yeast with a mammalian type sugar chain, recovering delay of growth and being excellent in thermotolerance and protein productivity as well as yeast with excellent beta-glucan productivity, after induction of useful mutations and repeating such useful mutations, by controlling proofreading function of DNA polymerase of a loss-of-function mutant of yeast such as a gene-disruptant of yeast or a gene-mutant of yeast. Namely, the present invention is based on an evidence that yeast suitable to produce protein and to produce beta-glucan can be obtained by causing pol3 gene or cdc6– gene to which mutation related to control of proofreading function is introduced to be expressed in yeast and by repeating culture.

That is, a first aspect of the present invention is related to a method for breeding yeast avoiding high temperature sensitivity or recovering growth activity including a step controlling proofreading function of DNA polymerase in a loss-of-function mutant of yeast such as a gene-disruptant of yeast or a gene-mutant of yeast and a method for breeding yeast which produces beta-glucan efficiently. A preferred embodiment of the present invention is the above-mentioned method for breeding yeast, wherein the yeast is a budding yeast (*Saccharomyces cerevisiae*). A preferred embodiment of the present invention is the above-mentioned method for breeding yeast wherein the yeast is a fission yeast (Schizosaccharomyces pombe). As proved by examples, yeast avoiding high temperature sensitivity or recovering growth activity, especially yeast which produces beta-glucan efficiently, can be bred by controlling a proofreading function of DNA polymerase in a gene-disruptant of yeast (especially och1 gene-disruptant and like that).

A preferred embodiment of the present invention is any one of the above-mentioned methods for breeding yeast, wherein the gene-disruptant of yeast is a strain which has one or more disruptions selected from a group of {och1 disruption, mnn1 disruption, mnn4 disruption and alg3 disruption} or a strain which has one or more mutations selected from a group of {och1 mutation, mnn1 mutation, mnn4 mutation and alg3 mutation}. That is, as proved by examples, yeast exerting productivity of mammalian type protein while avoiding high temperature sensitivity or recovering growth activity, especially yeast which produces beta-glucan efficiently, can be obtained by using a gene-disruptant whose och1 gene and the like related to elongation of a sugar chain was disrupted.

A preferred embodiment of the present invention is any one of the above-mentioned methods for breeding yeast, wherein the step of controlling the proofreading function of DNA polymerase is a step for controlling error prone frequency of DNA polymerase in a loss-of-function mutant of yeast such as a gene-disruptant of yeast or a gene-mutant of yeast, more specifically, any one of the above-mentioned methods for breeding yeast comprising a step of modifying amino acid sequence of Pol3 (for example, polypeptide described in sequence number 1) in a loss-of-function mutant such as a gene-disruptant of budding yeast. Moreover, a preferred embodiment of the present invention is any one of the above-mentioned methods for breeding yeast comprising a step of modifying amino acid sequence of Cdc6 (for example, polypeptide described in sequence number 7) in a loss-of-function mutant of fission yeast such as a gene-disruptant of fission yeast.

A preferred embodiment of the present invention relates to, as proved by the examples, any one of the above-mentioned methods for breeding yeast, wherein the gene-disruptant of yeast is a gene-disruptant of budding yeast in which och1 disruption, mnn1 disruption and mnn4 disruption were introduced, and wherein the step for controlling proofreading function of DNA polymerase includes a step for transforming the gene-disruptant of yeast with DNA of POL3 gene, which is shown in sequence number 2, wherein 962nd base A is substituted by C and 968th base A is substituted by C. This embodiment, as proved by using a budding yeast by the example which will be described later, can be regarded as being usable for yeast in general.

Moreover, a preferred embodiment, as proved by the example, relates to any one of the above-mentioned methods for breeding yeast, wherein the gene-disruptant of yeast is a gene-disruptant of fission yeast in which och1 disruption was introduced, and wherein the step for controlling proofreading function of DNA polymerase includes a step for transforming the gene-disruptant of yeast with DNA in which GAT ATT GAA that are 898th to 906th bases of cdc6+ gene shown in sequence number 8 are changed to GCC GGC GCT. A gene-disruptant of fission yeast in which och1 disruption was introduced may be a strain in which only och1 disruption was introduced or, for example, a strain which has one or more gene disruptions selected from a group of {mnn1 disruption, mnn4 disruption and alg3 disruption} or a strain which has one or more mutations selected from a group of {och1 mutation, mnn1 mutation, mnn4 mutation and alg3 mutation}.

A preferred embodiment of the present invention relates to any one of the above-mentioned methods for breeding yeast, wherein the yeast avoiding high temperature sensitivity or recovering growing activity is a budding yeast or a fission yeast that produces glycoprotein with a mammalian type sugar chain.

A preferred utilization embodiment of the present invention relates to a method for producing glycoprotein by culturing yeast obtained by any one of the above-mentioned methods for breeding yeast in a culture medium, making the yeast produce glycoprotein, and collecting the glycoprotein from the culture. A glycoprotein obtained by such a production method is, for example, one with mammalian type sugar chain, and can be effectively used for medicine and the like. A budding yeast or a fission yeast is listed as the yeast of this utilization embodiment. Likewise, a preferred utilization embodiment of the present invention relates to a method for producing beta-glucan by culturing yeast obtained by any one of the above-mentioned methods for breeding yeast in a culture medium, making the yeast produce beta-glucan, and collecting the beta-glucan from the culture. A beta-glucan obtained by such a production method, for example, can be effectively used for various functional foods, medicine and the like. A budding yeast or a fission yeast is listed as the yeast of this utilization embodiment.

A second aspect of the present invention relates to an yeast obtained by a method for breeding yeast avoiding high temperature sensitivity or recovering growth activity including a step for controlling proofreading function of DNA polymerase in a loss-of-function mutant of yeast such as a gene-disruptant of yeast or a gene-mutant of yeast and an yeast obtained by a method for breeding yeast which produces beta-glucan efficiently including a step for controlling proofreading function of DNA polymerase in a loss-of-function mutant of yeast. The yeast avoids high temperature sensitivity, recovers growth activity, produces beta-glucan efficiently and has good growth character despite being a loss-of-function mutant of yeast such as a gene-disruptant of yeast. A budding yeast or a fission yeast is listed as the yeast of this utilization embodiment.

As a specific yeast, an yeast deposited to the National Institute of Advanced Industrial Science and Technology Patent Organism Depositary as a deposit number of "FERM P-20956" or "FERM P-21145" can be mentioned. These yeasts avoid high temperature sensitivity or recover growth activity. Using these yeasts, protein similar to that of mammal can be produced. Also, these yeasts produce beta-glucan efficiently. That is, the present invention provides a method for producing glycoprotein or a method of producing beta-glucan using the yeast produced by any one of the above-mentioned methods or the deposited as "FERM P-20955", "FERM P-20956" or "FERM P-21145".

A third aspect of the present invention relates to a method for producing glycoprotein or a method of producing beta-glucan using the yeast produced by any one of the above-mentioned methods or any one of the above-mentioned yeasts. As proved by the example, these yeasts have an excellent productivity of glycoprotein and an excellent productivity of beta-glucan, so that glycoprotein or beta-glucan can be efficiently produced.

A fourth aspect of the present invention relates to a method for breeding yeast capable of foreign gene expression, comprising a step for controlling proofreading function in a loss-of-function mutant of yeast such as a gene-disruptant of yeast or a gene-mutant of yeast and obtaining foreign protein. That is, if a foreign gene, such as human gene etc. can be expressed using yeast, it is useful for development of medicine and the like. As proved by the example, in the present invention, yeast capable of foreign gene expression can be bred. In addition, the present invention of this aspect can adopt various utilization embodiments as the invention of the first aspect. A budding yeast or a fission yeast is listed as yeast of this utilization embodiment.

The present invention can provide a method for breeding a loss-of-function mutant of yeast such as a gene-disruptant (or a strain with a mutant gene) of yeast avoiding high temperature sensitivity or recovering growth activity, and an yeast obtained by such a method for breeding.

The present invention can provide a method for breeding a novel mutant strain of yeast keeping productivity of glycoprotein with a mammalian type sugar chain, recovering delay of growth and being excellent in thermotolerance and productivity of protein, and a method for breeding such a mutant strain.

The present invention can provide a method for producing glycoprotein with a mammalian type sugar chain using the above-mentioned method for breeding yeast avoiding high temperature sensitivity or recovering growth activity.

The present invention can provide a method for breeding yeast which produces beta-glucan efficiently and an yeast obtained by such a breeding method The present invention can provide a method for producing beta-glucan using the above-mentioned method of breeding yeast which produces beta-glucan efficiently.

The present invention can provide a method for breeding yeast having expression ability of a foreign protein and a method for producing foreign protein by such a method for breeding.

BEST MODE FOR CONDUCTING THE INVENTION

A first aspect of the present invention relates to a method for breeding yeast avoiding high temperature sensitivity or recovering growth activity, comprising a step for controlling proofreading function of DNA polymerase by using a loss-of-function mutant of yeast such as a gene-disruptant of yeast or a gene-mutant of yeast and a method for breeding yeast which produces beta-glucan efficiently. A second aspect of the present invention relates to an yeast produced according to such a method for breeding. Moreover, a preferred embodiment of the present invention is a method for producing glycoprotein with a mammalian type sugar chain or beta-glucan, including such a method for breeding yeast. It is to be noted that in the present specification, "loss-of-function mutant" means a strain incorporating either one of or both of gene-disruption and gene-mutation. However, a strain incorporating both of gene-disruption and gene-mutation is included in a gene-disruptant or a gene-mutant.

The yeast used in the present invention is not limited so long as it is commonly called as yeast, and budding yeast, fission yeast and the like can be used appropriately. As a typical yeast, those which belong to Saccharomycetaceae or Schizosaccharomycetaceae are included. As a more specific yeast, *Saccharomyces cerevisiae* which is a kind of budding yeast and Schizosaccharomyces pombe which is a kind of fission yeast, that are widely used for a model of eukaryote are included. As other yeasts used in the present invention, for example, Aureobasidium pullulans are included. Among these, budding yeast or fission yeast is preferable as proved in the examples, but the present invention is not limited to budding yeast or fission yeast particularly and can be applied to general yeast widely. Especially, about fission yeast, similar to budding yeast, by disrupting a specific gene, it is known to prevent an addition of mannose to a sugar chain effectively and to produce glycoprotein with a mammalian type sugar chain (Takehiko Yoko-o et al., FEBS letters 489 (2001) 75-80;

Clinton E. Ballow et al., Proc. Natl. Acad. Sci. USA Vol. 91. pp 9327-9331, 1994; Naotaka Tanaka et al., Biochemical and Biophysical Research Communications 330 (2005) 813-820; Sandra Fanchiotti et al., Journal of Cell Biology, Vol. 143, No. 3, 1988, pp 625-636). And about Pichia pastoris, for example, it is described in Wouter Vercken et al., Applied and Environmental Microbiology, Vol. 70, No. 5, 2004, pp 2639-2646, and about yeast Yarrowia Lipolyticam for example, it is described in Stephnie Barnay-Verdier et al., Microbiology (2004), 150, p 2185-2195. And in the present invention, as a gene involved in proofreading function of DNA polymerase which is modified for introduction of mutations is thought to be not so strongly related to genes associated with a sugar chain, by controlling proofreading function of DNA polymerase against gene-disruptants disclosed in these literatures or gene-disruptants easily obtained from these gene-disruptants by a person skilled in the art, yeast avoiding high temperature sensitivity or recovering growth activity can be thought to be obtained.

The gene-disruptant of yeast used in the present invention is not especially limited so long as it is a strain in which some gene in wild-type yeast was disrupted. A strain which has some gene disruption generally decreases thermotolerance and growth activity, compared to wild-type yeast. The present invention can provide a strain to which mutation is introduced by controlling proofreading function of DNA polymerase and which recovered decreased functions by genetic disruption. Moreover, function can be exerted which is absent or poor in wild-type strain by introducing mutations by controlling proofreading function of DNA polymerase. While examples shows, as will be described later, avoid of high temperature sensitivity and recovery of growth activity by using triple disruptant of budding yeast and fission yeast, the present invention is not limited to triple disruptant of budding yeast and fission yeast, as described above, but can be applied to various gene-disruptants of yeast. Hereinafter, specific gene-disruptants will be described.

A double disruptant (Δoch1 mnn1) with mnn1 disruption on OCH1 gene-disruptant (Δoch1) is disclosed in the Japanese patent 3091851 bulletin (see example 1 of the bulletin for example). That is, when a gene-disruptant of yeast used in the present invention is a double disruptant (Δoch1 mnn1), such a double disruptant may be obtained according to the method described in the bulletin. Further according to the bulletin, using such a double disruptant, core type sugar chain which is the same as high mannose produced by mammalian cells such as human cells, or glycoprotein of high mannose type having this sugar chain structure can be produced in large quantity and in high purity. It is thought that by using this double disruptant in a method for breeding yeast of the present invention, high temperature sensitivity is avoided and growth activity is recovered, so that core type sugar chain and the like which is the same as high mannose produced by mammalian cells can be produced effectively. In addition, in the bulletin, disruptants (Δoch1 mnn1 his1 and/or his3) etc. are disclosed and those can be included in a gene-disruptant of yeast in the present invention.

A triple disruptant Δoch1 mnn1 mnn6) with Δoch1 disruption, mnn1 disruption, and mnn6 disruption is disclosed in the Japanese patent 3091851 bulletin (for example, see example 1 of the bulletin). That is, in the case that a gene-disruptant of yeast used in the present invention is a triple disruptant (Δoch1 mnn1 mnn6) etc., such strains can be obtained by the method described in the bulletin. And according to the bulletin, using such triple disruptant etc., core type sugar chain which is the same as high mannose produced by mammalian cells such as human cells, or glycoprotein of high mannose type having this sugar chain structure can be produced in large quantity and in high purity. It is thought that by using these strains in a method for breeding yeast of the present invention, high temperature sensitivity is avoided and growth activity is recovered, so that core type sugar chain and the like which is the same as high mannose produced by mammalian cells can be produced effectively. In addition, in the bulletin, disruptants (Δoch1, mnn1, mnn6, his1 and/or his3, ura3) etc. are disclosed and those can be included in a gene-disruptant of yeast of the present invention. Moreover, according to techniques disclosed in the bulletin, double disruptant whose OCH1 gene and MNN1 gene were disrupted can be obtained.

Further a quadplex disruptant with disrupted function of MNN4 gene and KRE2 gene as well as Δoch1 and Δmnn1 disruption is disclosed in Japanese patent publication 1997-266792 bulletin. As disclosed in the bulletin, for example, by transferring diploid cells obtained by conjugating mutant strains of different conjugation types or gene-disruptants to a sporulation medium lacking nitrogen source [for example, see F. Sherman, Method in Enzymology, vol. 194, p 17 (1991)] meiosis is occurred, 4 spores produced by this were separated individually under a microscope and various mutant strains can be produced by checking their phenotype.

A triple disruptant with och1 disruption (Δoch1), mnn1 disruption (Δmnn1) and mnn4 disruption (Δmnn4) is disclosed in the international publication WO01/014522 bulletin. That is, a gene-disruptant of yeast is disclosed in which function of a gene coding for alpha-1,6 mannosyl transferase which conducts first elongation reaction (OCH1), a gene coding for alpha-1,3 mannosyl transferase which adds mannose to nonreducing end of sugar chain (MNN1) and a gene regulating addition of mannose-1-phosphate (MNN4) were disrupted among genes involved in biosynthesis of outer sugar chains specific to yeast. TIY20 used in the examples of the present invention, is different from TIY19 by mat disclosed in the bulletin and is obtained from the same clone by tetrad analysis. About tetrad analysis, it can be done, for example, according to Dan Burke et al. (Teiichi Oya et al. translated) experimental manual of yeast gene, Maruzen Co. Ltd. Issued on Dec. 10, 2002.

In international publication WO01/014522 pamphlet (patent literature 1), a disruptant of budding yeast in which disruptions including och1 disruption, mnn1 disruption, mnn4 disruption and alg3 disruption were introduced is disclosed and a disruptant of budding yeast whose OCH1 gene, MNN1 gene, MNN4 gene and ALG3 gene were disrupted is disclosed. And in the bulletin, besides those mutant traits due to gene-disruption, mutant of yeast having auxotrophy mutation trait selected from a group of ura3 mutation, his3 mutation, leu3 mutation, leu2 mutation, ade2 mutation, trp1 mutation and can1 mutation is disclosed. According to the bulletin, it is disclosed that these mutants can easily introduce foreign gene by using auxotrophy selection marker and that a mammalian type sugar chain or glycoprotein with a mammalian type sugar chain can be produced in large quantity and with high purity by using these mutants. Consequently, in a method for breeding yeast of the present invention, using a mutant strain disclosed in the bulletin, it is thought that mammalian type glycoprotein etc. can be produced efficiently as temperature sensitivity is avoided and growth activity is recovered. Moreover, it is thought that mutants thus having temperature sensitivity avoided and growth activity recovered produce beta-glucan efficiently.

Consequently, for example, as a loss-of-function mutant of yeast such as a gene-disruptant of yeast or a gene-mutant of yeast, a strain having one or more disruption selected from a group consisting of {och1 disruption, mnn1 disruption, mnn4 disruption and alg3 disruption} or a strain having one or more mutations selected from a group consisting of {och1 mutation, mnn1 mutation, mnn4 mutation and alg3 mutation} can be mentioned. Namely, a problem similar to that described above is present not only in a gene-disruptant whose loss of specific gene function is due to a gene-disruption but also in a gene-mutant due to a gene-mutation, so that yeast having avoided high temperature sensitivity and recovered growth activity can be obtained by controlling proofreading function of DNA polymerase, whereby beta-glucan can be produced efficiently. Among loss-of-function mutants of yeast such as gene-disruptants of yeast or gene-mutants of yeast, gene-disruptants of yeast with only och1 disruption or och1 disruption together with other mutations are preferably used. In addition, in Japanese publication of patent application 2001-161376 och1 disruptant of fission yeast (Δoch1) whose sugar transfer enzyme och1+ function is lost is disclosed. In the present invention, as a gene-disruptant of yeast, och1 disruptant of fission yeast ((Δoch1) can be used. Consequently, for example, even when a fission yeast is used as the yeast, a gene disruptant with only och1 disruption or och1 disruption together with other mutations can be preferably used.

A Step for Controlling Proofreading Function of DNA Polymerase

As a step for controlling proofreading function of DNA polymerase in a loss-of-function mutant of yeast such as a gene-disruptant of yeast or a gene-mutant of yeast, what contains a step for controlling error prone frequency of DNA polymerase in a gene disrupted yeast strain is included and more specifically, what contains a step modifying amino acid sequence of Pol3 in a loss-of-function mutant of budding yeast such as a gene-disruptant of budding yeast is included. And what contains a step modifying amino acid sequence of cdc6 in a loss-of-function mutant of fission yeast such as a gene-disruptant of fission yeast is included.

In this specification, "error prone frequency" means level of character of error prone. Error prone frequency, for example, is expressed by absolute number of mutations (number of mutation point itself) or by relative number (ratio of mutation number in full-length) in gene sequences. Alternatively, when referring to an organism or enzyme, error prone frequency may be expressed by absolute number or relative number of mutations in gene sequences per a reproduction or a division of an organism. In the absence of a specific reference, error prone frequency is expressed by a number of error in gene sequence per one replication process. Error prone frequency may be named as "fidelity" as a reverse index in this specification. "Error prone frequency is even" means that error prone frequencies are substantially equal to each other when referring to factors (polymerase etc.) performing gene replication. On the other hand, "error prone frequency is uneven" means the case that significant difference exists in factors (polymerase etc.) performing gene replication.

In the present invention, "control of error prone frequency" means to change error prone frequency. While such control of error prone frequency includes increase and decrease of error prone frequency, increase of error prone frequency is more preferable. As a method for controlling error prone frequency, for example, modification of DNA polymerase which has proofreading function, insertion of inhibiting or repressing factor of polymerization or elongation reaction during replication, inhibition or repression of a factor which promotes these reaction, loss of single or multiple base(s), loss of DNA repair enzyme, modification of an enzyme comprising a function of removing and repairing an abnormal base, modification of repair factor of mismatched base pairing, decrease of fidelity of replication itself etc. can be mentioned, but not limited to these. Control of error prone frequency may be done to both strands of double stranded DNA and may be done to one strand. Control of error prone frequency done to only one strand of double stranded DNA is preferable because an induction of a toxic mutation is reduced.

In the present specification, "error prone" means character of misincorporation rate in gene (DNA) replication (that is, of replication error). Error prone is influenced by fidelity of proofreading function of enzyme comprising proofreading function (for example, DNA polymerase). In this specification "replication error" means misincorporation of nucleotide during replication of genes (DNA etc.). Replication error is extremely low in living organisms generally at the frequency of once in $10^8$ to $10^{12}$ times. The reasons of low frequency of replication error include the fact that replication is initiated by having complementary base pairing formed between template DNA and incorporated nucleotide in the nucleotide incorporation and that there is a function that proofreading function of DNA polymerase etc., that is, 3'→5' exonuclease detect misincorporation and immediately cut out the nucleotide that is not complementary to template when misincorporated. Therefore, in the present invention, a control of error prone frequency at the replication can be done by disorder of specific base pairing, disorder of proofreading function etc.

In this specification, "error free" means there is few misincorporation at the gene (DNA etc.) replication, more preferably, a character with substantially no misincorporation. Error free is mainly influenced by the fidelity of proofreading function of enzyme comprising proofreading function. In the present specification, error prone and error free can be classified absolutely (that is, determined by level of error prone frequency etc.) or relatively (for error prone frequencies in factors assuming replication of 2 or more types of genes (for example, DNA polymerase etc.), the higher can be classified as error prone and the lower can be classified as error free.

In addition, "DNA polymerase" means an enzyme comprising function polymerizing DNA and releasing pyrophosphate from 4 kinds of deoxyribonucleoside 5'-triphosphates, wherein Pol3 of budding yeast and Cdc6 of fission yeast are included. For DNA polymerase reaction, template DNA, primer molecule, $Mg^{2+}$ etc. are required. Molecular strand is elongated by sequentially adding nucleotides complementary to template at the 3'-OH end of primer.

In the present invention, for controlling proofreading function of DNA polymerase, by some method, it is only necessary to make yeast cells disequilibrium mutator. To make yeast cell disequilibrium mutator, it is only necessary to disrupt a gene involved in proofreading function of DNA polymerase among DNA polymerase genes or to introduce some mutation in such genes according to known method. Method for gene disruption or introduction of mutation in a gene is, for example, because gene regions involved in proofreading function among DNA polymerase genes is known, DNA sequence of those gene regions has only to be replaced, for example, by 1 to 100 other base(s), preferably 1 to 10 other base(s), more preferably 1 to 3 other bases(s) for transformation. For example, yeast cells can be made disequilibrium mutators by expression in target yeast cells of mutant protein with eliminated proofreading function of polymerase δ (Polδ) which is involved in replication of lagging strand at eukaryotic chromosome DNA replication. That is, methods for expression of Polδ mutant protein in target yeast cells include one in which polδ mutant genes are obtained artificially, having mutant gene expressed and functioned by transformation into target yeast. That is, as a method for producing mutant type Pol3 that is a Polδ in budding yeast with eliminated proofreading function, proofreading function may be controlled by replacing a part of amino acid sequence of active site of the proofreading function artificially using POL3 gene as template which is cloned in advance. In addition, from a strain which has the same trait as pol3 mutant and which was already identified as natural mutant, the mutant gene can be cloned and used (in following examples the latter method was used). A gene of DNA polymerase may include not only structure gene of DNA polymerase, but also both regulatory sequences of transcription and/or translation such as promoter of DNA polymerase.

And as another example, yeast cells can be made disequilibrium mutators by expression in target yeast cells of mutant protein with eliminated proofreading functions of Cdc6 (Cell division cycle 6) which a Polδ in fission yeast. That is, methods for expressing Cdc6 mutant protein in target yeast cells include one in which cdc6 mutant gene is obtained artificially, having mutant gene expressed and functioned by transformation into target yeast. Specifically, by the same production method as the pol3 mutant gene, cdc6 (cdc6−) of mutant type with eliminated proofreading function can be obtained.

In the following examples, pol3-01 mutant gene of POL3 gene comprising DNA sequence shown in sequence number 2 is what base A of 962nd in POL3 gene shown in sequence number 2 is substituted by C, 968th base A is substituted for C. However, method for controlling proofreading function of DNA polymerase in budding yeast is not limited to the above-mentioned methods and includes various methods such as a method, for example, including replacement at the above position, that base sequence of other position are replaced by the number of 1 to 10 (preferably 2 to 5, more preferably 2 to 5 of 898th to 980th of POL3 gene shown in sequence number 2). Additionally, cdc6-1 mutant gene (shown in sequence number 10) in cdc6+ gene comprising a sequence shown in sequence number 8 is that 898th to 906th bases GAT ATT GAA in cdc6+ shown in sequence number 8 is replaced to GCC GGC GCT. However, method for controlling proofreading function of DNA polymerase in fission yeast is not limited to above-mentioned method but for example, method including a replacement at the above-mentioned positions and replacing 1 to ten of nucleotide sequence of other positions (preferably 2 to 5, more preferably 2 to 5 of 898th to 980th nucleotide of cdc6+ gene shown in sequence number 8).

In this specification, proofreading function is "lower than that of wild-type" means proofreading function is lower than its wild-type enzyme (that is, a number of mutations which remains after proofreading treatment by the enzyme is more than a number of mutations which remain after proofreading treatment by wild-type enzyme) when it is mentioned about an enzyme having a proofreading function. Such comparison with wild-type can be described by relative or absolute description. Such comparison can also be done by error-prone frequency etc.

In this specification, "mutation" means, as stating about genes, occurrence of change of the gene sequence or a status of a sequence of the gene (nucleic acid of amino acid) occurred by the change. In this specification, for example, mutation is used for a change of gene sequence on proofreading function. In this specification, if not specifically stated, mutation is used in the same meaning as modification.

To make a useful mutant, mutagenesis in organisms is most common. Mutation generally means a change of gene sequence that codes genes and includes a change of DNA sequence. Mutation is largely classified, by effects on a solid object where the mutation is generated, into following 3 kinds: A) neutral mutation: most mutation corresponds to this mutation and has little effect on growth and metabolism of organisms. B) Deleterious mutation: this mutation occurs fewer than neutral mutation. It inhibits growth or metabolism of organisms. Deleterious mutation includes lethal mutation that disrupts genes essential to growth and development. In the case of microorganisms, while depending on species, rate of deleterious mutation in all mutation is generally estimated about ⅟10 to ⅟100. C) Beneficial mutation: this mutation is beneficial for breeding organisms. Its frequency of occurrence is extremely low compared to that of neutral mutation. Consequently, to obtain an individual of organism having introduced beneficial mutation, large population of living organisms and long time are required. In addition, sufficient effect of breeding of organisms rarely appears from a single mutation and accumulation of multiple beneficial mutations is often necessary. As well, the introduction of these mutations, for example, can be done according to the method described in Dan Burke et al. (translated by Teiichi Oya) Experimental manual of a yeast gene, Maruzen Co. Ltd. Heisei 14, December 10 issued etc.

In what follows, a case in which POL3 gene was used as a gene controlling proofreading function of DNA polymerase, whereby yeast cells are made disequilibrium mutators is explained. In addition, yeast cells can be made disequilibrium mutators in the case of using cdc6 gene of fission yeast as a gene controlling proofreading function of DNA polymerase, in the same way as the case using POL3 gene. In addition, Pol3 and cdc6 are DNA replication enzyme designated as polymerase delta (Polδ) in eukaryotic organism that correspond to Polδ in budding yeast and fission yeast respectively. Specifically, POL3 gene can be obtained by PCR method using, as a template, genome obtained from budding yeast (Saccharomyces cerevisiae) strain W303-1A (ura3, leu2, his3, trp1, ade2) (Kainuma et al. Glycobiology, Vol. 9. 133-141 (1999)). As a primer, restriction site added primer may preferably be used for easily cutting out a part coding for Pol3 protein. Specifically explaining, after cloning POL3 gene of budding yeast in an appropriate vector, primers are designed for introducing mutation controlling proofreading function of Pol3 and mutant type pol3 can be obtained.

And to express above-mentioned mutant pol3 in yeast, by inserting promoter in upstream and terminator in downstream, expression cassette may be constructed which may be inserted to expression vector. And if promoter and terminator have already existed in expression vector for introducing the gene, without construction of expression cassette, utilizing the promoter and terminator, only the fused gene can be introduced between them.

While the promoter in the expression cassette is not limited so long as being used in yeast expression system generally and being able to express the gene in transformed yeast cells, for example, PGK, GAP, TP1, GAL1, GAL10, ADH2, PHO5 and CUP1 etc. are included. Among these, GAP promoter is preferable.

On the other hand, the terminator may be one used in yeast expression system generally and enabling termination of transcription by being present in downstream of an introduced fused gene and for example, including ADH1, TDH1, TFF, TRP5 and the like.

The expression vector in which an expression cassette is inserted it is not particularly limited so long as being one which is used for yeast expression system generally. As specific expression vectors, plasmids from *Escherichia coli* (for example, pBR322, pBR325, pUC12 and pUC13), plasmids from *Bacillus subtilis* (for example, pUB110, pTP5 and pC194), plasmids from yeast (for example, pSH19 and pSH15), bacteriophage such as λ phage etc., animal viruses such as retrovirus, vaccinia virus etc. and insect disease viruses such as baculovirus etc. can be used but plasmids from yeast can be used preferably.

While plasmids utilized for transformation of yeast are not limited so long as plasmids can be used for yeast transformation, for example, yeast episome plasmid abbreviated as YEp, yeast replicating plasmid abbreviated as YRp etc. are included. Yeast episome plasmid vector contains 2 micro plasmid sequence which is contained in yeast primarily and is a vector which can be replicated in host yeast cells utilizing the replication origin. Yeast episome expression vector is preferred to contain at least ARS sequence of 2 micro plasmid sequence and capable to replicate outside of chromosome in host yeast cells. As specific plasmid, Yep51, pYES2, Yep351, Yep352 and pREP etc. are included.

As an yeast episome type expression vector, a shuttle vector which can replicate in *Escherichia coli* is preferable to subclone in recombinant *Escherichia coli*, and one which includes a selectable marker such as an ampicillin resistant gene etc. is more preferable. And the expression vector includes marker gene which can be used for selection of yeast clones by nutrient requirement or drug resistant. As marker gene, for example, HIS3, TRP1, LEU2, URA3, ADE2, CAN1, SUC2, LYS2 and CUP1 etc. are included (edited by Yasuji Oshima, Experimental methods for biochemistry 39, Experimental methods for yeast molecular genetics, 119-144 (1996)). These are just examples and can be selected appropriately according to genotype of a host yeast strain for gene introduction. The series of techniques relating to construction of above-mentioned gene expression vector can be conducted by a person skilled in the art appropriately referring to following examples or by techniques in common use.

To an expression vector, a promoter, an enhancer, a splicing signal, a polyA addition signal, a selectable marker, a replication origin of SV40 and DNA coding for tag etc. can be added. And expression vectors may be fusion protein expression vectors. As fusion protein expression vectors available in the market, pGEX series (Amersham Pharmacia Biotech company), pET CBD Fusion System 34b-38b (Novagen company), pET Dsb Fusion Systems 39b and 40b (Novagen company), and pET GST Fusion System 41 and 42 (Novagene company) are included.

In the present invention, host yeast transformed with the above-mentioned mutant pol3 expression vector (mutator) includes to use yeast belonging to *Saccharomyces*, *Candida* but not limited to these specifically. As yeast of *Saccharomyces*, for example, *Saccharomyces cerevisiae* KK4 strain, Y334 strain, Inv-Sc1 strain and W303 are included. And in the present invention, as host yeast transformed with the mutant cdc6 gene expression vector, yeast belonging to Shizosaccharomyces or *Candida* is included but not limited to particularly. As yeast of Shizosaccharomyce, for example, Shizosaccharomyces pombe and TN8 strain are included.

Following methods are included, for example, for transformation of yeast with fusion gene expression vector. Methods such as a method to treat with lithium phosphate and to incubate adding DNA and PEG, and electroporation method etc. are included (Becker and Guarente, Methods Enzymol., 194, 182-187 (1991)). And spheroplast method in which spheroplast cells whose cell walls were digested by enzyme, PEG and DNA are incubated in the presence of calcium ion from calcium chloride (Hinnen et al., Proc. Natl. Acad. Sci. USA, 75:1929 (1978)) and a transformation method by bombardment of particles coated with DNA to cells (Fox T. D. et al., 1988. Plasmids can stably transform yeast mitochondria lacking endogenous mt DNA. Proc. Nat. Acad. Sci. 85:7288-7292) can be used.

Transformation of yeast may be done by the method including a step maintaining log phase yeast cells in a solution containing gene for introduction to the yeast cell and polyethylene glycol (Japanese patent 3682530).

Appropriate selectable markers are used for screening of transgenic yeast. For example, it is desirable to use a gene which is involved in metabolism on chromosomal DNA of host cells. That is, using host cells in which the gene on chromosomal DNA does not function by an appropriate method such as a mutation etc., by transformation with an expression vector including a corresponding normal gene, it is desirable that can be used for screening by growing only transformant cells containing a normal metabolic gene. Specifically, a selectable marker gene such as above-mentioned URA3, LEU2 etc. which are widely used is ligated to an expression vector. These genes may be selectable markers for screening in the case of chromosomal integration type (YIP type).

To introduce many mutations to transformed transgenic yeast, it is cultured to repeat divisions over several generations. Specifically, it is cultured in 5 ml medium overnight, scale-up culture is repeated such as 2 ml, 50 ml, 100 ml, and culture is repeated in the condition in which yeast can divide for about 1 week. As a culture method of transgenic yeast, it can be done according to a normal method used for yeast culture. As a medium, a medium is used so long as it contains carbon source assimilable for yeast, nitrogen source, inorganic salts etc. and transformant can be cultured effectively, specifically, YPD medium, YPG medium, YPDG medium, YPAD medium, glucose minimum medium (SD), iodide added minimum medium (SMM), Hartwell complete medium (HC), GAL fermentation test medium, or sporulation medium etc. can be used appropriately. And for example, synthetic medium (including carbon source, nitrogen source, inorganic source, amino acid, vitamin etc.) can be utilized which is added with various medium content supplied by Difco Company and from which amino acids are removed which can be supplied by a marker necessary for replication and maintenance of plasmid (Sherman, Methods Enzymol., 194, 3-57 (1991)).

To adjust pH of a medium between 6 and 8 is appropriate. Adjustment of pH is done by regulating additive amount of inorganic or organic acid, alkaline solution, urea, calcium carbonate and ammonia etc. Culture may preferably done at 28 degrees C. to 32 degrees C., preferably 30 degrees C. for about 1 week (for example, 1 day to 1 month, preferably 5 days to 10 days) with aeration or agitation appropriately. Especially, although to culture at 30 degrees C. adding KCl and sorbitol to culture TIY20 strain effectively is preferable, culture may be done without addition of KCl and sorbitol for adding moderate selection pressure. In addition, it may be cultured at a little higher temperature than 30 degrees C. such as 31 degrees C. to 35 degrees C. (or 32 degrees C. to 33 degrees C.) etc.

An Yeast Avoiding High Temperature Sensitivity or Recovering Growth Activity

An yeast avoiding high temperature sensitivity or recovering growth activity means the yeast which was produced by the above-mentioned method. And specifically, it includes budding yeast or fission yeast producing glycoprotein having a mammalian type sugar chain. More specifically, it includes yeast obtained by modifying genes related to proofreading function of DNA polymerase in a known gene-disruptant or a known gene-disruptant which can be produced by a known method from a known gene-disruptant.

A Glycoprotein Having Mammalian Type Sugar Chain

A glycoprotein having mammalian type sugar chain may preferably be at least one which is produced by a known gene-disruptant as described above. As for a method for isolating and/or purifying glycoprotein from a gene-disruptant, the method disclosed in any of literatures described in this specification or a known method can be used as appropriate. For example, after culture, cells are collected by centrifugation and are suspended in a water type buffer. After that, cells are crushed using an ultrasonic crusher, a French press, a homogenizer or a dynomill appropriately and cell free extract is obtained. The cell free extract obtained as above is centrifuged and supernatant is recovered. As extraction method from the supernatant, solvent extraction method, salting-out method by ammonium sulfate, precipitation by organic solvent, anion exchange chromatography using resin such as diethylaminoethyl-sepharose etc., affinity chromatography method can be combined appropriately.

In this specification, Man represents mannose and GlcNAc represents N-acetyl glucosamine. And asterisk represents phosphorylation site. As a specific glycoprotein having mammalian type sugar chain, glycoprotein with oligo saccharide chain shown in the following formula (I), or (II) as asparagine-linked sugar chain are included.

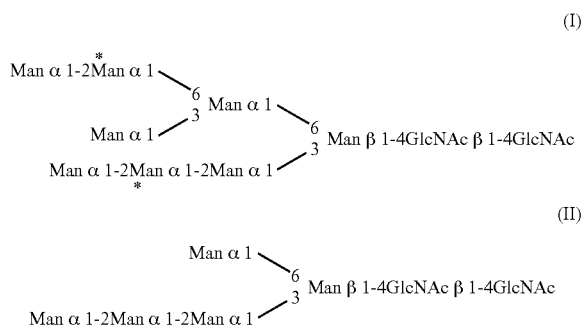

An Yeast Which Produces Beta-Glucan Efficiently

An yeast which produces beta-glucan efficiently includes, in the same way as the yeast avoiding high temperature sensitivity or recovering growth activity, the yeast which was produced by the above-mentioned method. On the other hand, it is thought that beta-glucan may be obtained efficiently by using yeast avoiding high temperature sensitivity or recovering growth activity without controlling proofreading function of DNA polymerase in a gene-disruptant of yeast. As an example of yeast which produces beta-glucan efficiently, a budding yeast or a fission yeast which produces beta-glucan efficiently can be mentioned. More specifically, it includes yeast obtained by modifying genes related to proofreading function of DNA polymerase in a known gene-disruptant or a gene-disruptant produced according to a known method from a known gene-disruptant.

Beta-Glucan

Beta-glucan may preferably be at least one which is produced by the above-mentioned known gene-disruptant. For example, as a specific type of beta-glucan, beta-1, 3-D-glucan and beta-1, 6/1, 3-D glucan can be mentioned. As a method for isolating and/or purifying beta-glucan from a gene-disruptant (especially from cell wall of yeast), a known method may be used as appropriate. For example after completing culture, the obtained culture (cell) is collected by centrifugation, and suspended in water type buffer. Thereafter, cells are crushed by using a ultrasonic crusher, a vortex mixer, a French press, a homogenizer, a dynomill and the like as appropriate, whereby cell lysate is obtained. The obtained cell lysate is centrifuged and pellets (including cell wall) are obtained, whereby resuspension, centrifugation and pellet collection are repeated for a number of times as appropriate. Thereafter, predetermined operations such as solvent elimination, reduced-pressure drying and resuspension are performed before performing, for example, a preferable method of carbohydrate analysis using HPLC by pyridylamino (PA) method and the like, where HPLC analysis by the PA method is more preferable.

The second aspect of the present invention relates to a method for breeding yeast having foreign gene expression ability including a step controlling proofreading function of DNA polymerase in a gene-disruptant of yeast. The second aspect of the present invention is the same as the first aspect other than using a gene-disruptant introduced with a foreign gene. A method for breeding a gene-disruptant introduced with a foreign gene is conducted according to methods of public domain appropriately. Although a foreign gene in the second aspect of the present invention is not limited particularly, if it is not a gene from the species, human alpha-galactosidase A gene from human is included for example. As proved by following example 5, a foreign gene can be expressed effectively according to the method. The second aspect of the present invention provides, as the first aspect, not only a method for breeding yeast having foreign gene expression ability but also yeast which has a foreign gene expression ability foreign gene and protein etc. produced by the method for breeding. Also, the invention according to this aspect provides a method for producing foreign protein effectively by culturing the yeast obtained by the above-mentioned method for breeding on a culture media, having foreign protein generated by expression of foreign gene and extracting foreign protein generated from the culture obtained.

Description of Sequence Number

Sequences described in sequence table in this specification indicate following sequences:

Sequence number 1 shows amino acid sequence of Pol3.

Sequence number 2 shows nucleotide sequence of cDNA coding for POL3 gene.

Sequence number 3 shows amino acid sequence of pol3-01.

Sequence number 4 shows nucleotide sequence of cDNA coding for pol3-01 mutant gene.

Sequence number 5 shows nucleotide sequence of forward primer used in PCR reaction in example 1.

Sequence number 6 shows nucleotide sequence of reverse primer used in PCR reaction in example 1.

Sequence number 7 shows amino acid sequence of Cdc6.

Sequence number 8 shows nucleotide sequence of cDNA coding for cdc6+ gene.

Sequence number 9 shows amino acid sequence of cdc-6-1.

Sequence number 10 shows nucleotide sequence of cDNA coding for cdc6-1 mutant gene.

Sequence number 11 shows nucleotide sequence of forward primer used in PCR reaction in example 6.

Sequence number 12 shows nucleotide sequence of reverse primer used in PCR reaction in example 6.

Sequence number 13 shows nucleotide sequence of forward primer used in PCR reaction in example 6.

Sequence number 14 shows nucleotide sequence of reverse primer used in PCR reaction in example 6.

Description of deposited strains

The YAB 100 strain obtained in a following example is deposited at the National Institute of Advanced Industrial Science and Technology International Patent Organism Depositary (AIST Tsukuba Central 6, 1-1, Higashi 1-chome Tsukuba-shi Ibaraki-ken 305-8566, Japan) as a deposit having an accession number of FERM BP-11122 on Jul. 11, 2006.

The YAB101 strain obtained in a following example is deposited at the National Institute of Advanced Industrial Science and Technology International Patent Organism Depositary (AIST Tsukuba Central 6, 1-1, Higashi 1-chome Tsukuba-shi Ibaraki-ken 305-8566, Japan) as a deposit having an accession number of FERM BP-11123 on Jul. 11, 2006.

The C2-11 (also referred to as YPAB100) strain obtained in a following example is deposited at the National Institute of Advanced Industrial Science and Technology International Patent Organism Depositary (AIST Tsukuba Central 6, 1-1, Higashi 1-chome Tsukuba-shi Ibaraki-ken 305-8566, Japan) as a deposit having an accession number of FERM BP-11124 on Dec. 27, 2006.

While the present invention is described in detail using examples next, the present invention is not limited to these examples.

Example 1

Construction of Plasmid pAB100 Inserted Mutated pol3 DNA Fragment

As follows, plasmid pAB100 (see FIG. 1(a)) was constructed by inserting a mutated pol3 fragment into SacI-SalI site of multicopy expression vector YEP352GAP2 for forced expression in budding yeast. Amino acid sequence of Pol3 is shown in sequence number 1 and DNA sequence coding Pol3 is shown in sequence number 2. A pol3-01 mutant gene obtained by this example is one in which 962nd base A in sequence number 2 is substituted by C and in which 968th base A in sequence number 2 is substituted by C. That is to say, a mutation was introduced in which amino acid residue coded by DNA sequence from 961st to 969th shown in sequence number 2 has DIE substituted by AIA. Thus obtained amino acid sequence of pol3-01 is shown in sequence number 3 and DNA sequence coding pol3-01 mutant gene is shown in DNA sequence 4. To explain it specifically, using genome of AMY128-1 strain (MAT α pol3-01, ura3-52, leu2-1, lys1-1, ade2-1, his1-7, hom3-10, trp1-289) which is known as natural mutator strain as template, pol3-01 mutant gene was amplified by PCR reaction (forward primer: 5'-AGCTCGAGCTC (SacI) ATGAGT-GAAAAAAGATCCCTTCCCATG-3' (sequence number 5), reverse primer: 5'-GCATCGCGGCCGC (NotI) TTAC-CATTTGCTTAATTGTTCTAC-3' (sequence number 6)) and the amplified fragment was cloned with SacI-NotI site in pYES2 vector (the obtained plasmid was designated as pYES2-pol3-01). Moreover, to express the pol3-01 mutant gene under the control of GAPDH promoter, pol3-01 mutant gene was digested with restriction enzymes SacI and XhoI from pYES2-Pol3-01 and was cloned with SacI-SalI site in YEp352 GAP-II vector (thus obtained plasmid was designated pAB100).

Isolation of a Thermotolerant Strain from a Sugar Chain-Modified Strain

Plasmid pAB100 obtained as above was transformed to a sugar chain-modified strain TIY20 (mat α och1::hisG mnn1:: hisG mnn4::hisG) of budding yeast (*Saccharomyces cerevisiae*). TIY20 was obtained by tetrad analysis from the same clone as TIY19 shown in the international publication WO01/ 014522 pamphlet (patent literature 1). Obtained transformants (TIY20/pAB100) was cultured in a synthetic medium SD-U (6.7 g of Yeast nitrogen base without amino acids (Difco laboratories), 20 g of glucose, 0.77 g of CMS-URA (Sunrise Science Products)) (liquid) for budding yeast to introduce more mutation regulating condition to enable division as much as possible. To obtain thermotolerant strains from these transformants, it was plated and cultured on SD-U solid medium at 37 degrees C. for 3 days and appeared colonies were picked up. To cure pAB100 from obtained strains, they were streaked on complete medium YPAD (10 g of Yeast extract (Difco laboratories), 20 g of peptone (Difco), 0.2 g of adenine sulfate (Sigma), 20 g of Glucose/IL), cultured and collected 20 single colonies each. Colonies which can not grow on SD-U medium were isolated from these colonies.

Analysis of Sugar Chain Length which is Added to Yeast Invertase

To measure N-linked sugar chain length of 9 strains (C15, C27, C28, C30, C3-20, C4-1, C3-3-1, C3-7-2 and C3-3-9) obtained in example 1, the length of N-linked sugar chain, which was added to invertase produced in yeast, was measured as follows. After each strain was cultured in 5 ml YPAD, it was cultured in 5 ml YPSuc (10 g of Yeast extract (Difco laboratories), 20 g of peptone (Difco), and 10 g of sucrose/1 L) for more than 3 hours and yeast cells were collected. The collected yeast cells were broken using vortex by adding 50 micro litter of SDS-PAGE sample buffer (15% Glycerol, 0.125M Tris-HCl (pH6.8), 2 mM PMSF, 3% SDS, 0.1% Bromophenol blue, 1% 2-mercaptoethanol) and glass beads. After centrifugation for 5 min at 15,000 rpm, each 5 micro litter of supernatant was electrophoresed by 5% SDS-PAGE (100V, 3 hours). The gel was transferred to reaction solution (3.4 g of sucrose, 3 ml of 3 M Na-acetate/100 ml), incubated at 37 degrees C. for 30 minutes and was washed twice using deionized water. It was transferred in staining solution (2 g of NaOH, 50 mg of triphenyltetrazoliumchloride/50 ml) and was boiled until color developed. The results are shown in FIG. 2. FIG. 2 is a photo of SDS gel electrophoresis as an alternative of drawings to measure N-linked sugar chain length. Lane of FIG. 2 shows, from the left, C15, C27, C28, C30, C3-20, C4-1, C3-3-1, C3-7-2, C3-3-9, TIY20 and W303-1A. From FIG. 2, it is elucidated that an N-linked sugar chain being added to invertase of 9 strains obtained have the same sugar chain length as a parent strain, TIY20.

Analysis of Growth Recovery Rate

Next, growth recovery rate of the strain obtained in example 1 was analyzed. It was cultured in 5 ml of YPAD at 30 degrees C., transferred to 10 ml of YPAD so as to adjust OD600 to 0.1 and cultured at 30 degrees C. or 37 degrees C. Yeast cells were collected and OD600 was measured at each timepoint. The results are shown in FIG. 3. FIG. 3 is a graph as an alternative of a figure showing growth recovery rate of 30 degrees C. and 37 degrees C. From FIG. 3, it is understood that about C4-1 and C3-20 of 9 strains which were analyzed showed the growth rate at 30 degrees C. exceeds that of TIY20. It is also understood from FIG. 3 that growth ability is to be recovered in C4-1 and C3-20 at 37 degrees C. though TIY20 grows little. In addition, appearance of each strain is shown in FIG. 1(b) and fraction of FIG. 1(b) is shown in FIG. 1(c).

Example 3

Analysis of Sugar Chain Structure

Sugar chain structure of mannoprotein in the strain obtained in example 1 was analyzed. The yeast cultured in 50 ml scale was collected, and was washed with water. Then, the yeast was suspended in 8 ml of 100 mM citrate buffer (pH7.0) and was autoclaved at 121 degrees C. for 2 hours. Supernatant was recovered by centrifugation, was added with 24 ml of cold ethanol and stand for 30 min. at −20 degrees C. After standing, the supernatant was centrifuged and its precipitation was recovered. The precipitation was suspended in water. Protein solution was prepared to 3 mg/ml and was treated with 5 micro litter of Glycopeptidase F (Takara Bio Co. Inc. 4450). After incubation at 37 degrees C. for 17 hours, it was added with water to 100 micro litter, was added with phenol:chloroform:isoamylalcohol (25:24:1), was mixed well and supernatant was recovered by centrifugation (extraction of phenol/chloroform). After chloroform was added to recovered solution and stirred, supernatant was recovered by centrifugation (chloroform extraction) and was dried up. After the dry-upped sample was pyrisylaminated by Pyridylamination manual kit (manufactured by Takara Bio Inc. 4480), extra reagent was removed by 7 times phenol/chloroform extraction. After chloroform extraction, the supernatant was dried up, redissolved in water and sugar chain structure was analyzed by HPLC (manufactured by Shimazu Co. Class-VP, column TOSOH TSK-GEL AMIDE-80 (Φ4.6 mm×250 mm), flow rate 1 ml/min, detection, 320 nm (excitation), 400 nm (fluorescent), buffer A, acetonitrile, buffer B, 200 mM TEAA (each sugar was eluted by increasing buffer concentration), gradient condition of buffer B, 0-40 min, 30 to 60%, 40-50 min, 30%). The result is shown in FIG. 4. FIG. 4 shows a graph showing the result of column analysis as an alternative of figure for analysis of sugar chain structure. In the figure, a number of mannose is shown by M. The vertical line is fluorescent intensity and the horizontal line is retention time (minute). From FIG. 4, wild-type strain, W303-1 A shows addition of various number of mannose. On the other hand, from FIG. 4, in all clones obtained, a peak was observed as a main peak which shows a sugar chain structure contained 8 mannoses the same as a parent strain TIY20. This indicates the mutant in the example has so-called mammalian type sugar chain structure. That is, a protein which has a desirable sugar chain can be obtained if the mutant strain in the example is used. That is to say, the present invention also provides a production method for a protein using the mutant strain in the example.

Example 4

Chitinase Analysis

An efficiency of secretion of the protein secreted from the strain obtained in example 1 was analyzed. To supernatant of 40 ml culture yeast, 40 mg of wet chitin (Sigma) was added and stirred overnight at 4 degrees C. Chitin was recovered by centrifugation and was washed 3 times with PBS. It was suspended in 100 micro litter of SDS-PAGE sample buffer, treated at 100 degrees C. for 10 min, 10 micro litter of the chitin was electrophoresed by SDS-PAGE and lectin blotted using ConA-biotin (Seikagaku Kogyo Co.). The blotting was detected using by Streptaridin-HRP (Seikagaku Kogyo) As a detection reagent, Immobilon Western Chemiluminescent HRP Substrate (Millipore) was used and Fuji film LAS1000 was used as a detection apparatus. The result is shown in FIG. 5. FIG. 5 is a graph as an alternative of a figure to show a secretion efficiency of protein which is secreted from the mutant strain. From FIG. 5, although the efficiency of secretion is 50% of that of wild-type in TIY20, it is understood that the secretion efficiency of the strain obtained is recovered. Above all, secretion efficiencies of C4-1 and C3-20 are recovered to the same level as the wild-type strain. Consequently, obtained strains C4-1 and C3-20 were deposited to the Patent Microorganisms Depositary as YAB100 and YAB101 respectively.

Activity Assay of Alpha-Galactosidase A (Investigation of Expression Ability of Foreign Gene)

C4-1, C3-20, C3-7-2 and C27 were transformed respectively with a vector (pRS4-GAP-alpha Gala) (Chiba, Y. et al., Glycobiology, 12, 821-828, 2002) which has an expression cassette in which human alpha-galactosidase A gene was ligated at the downstream of GAPDH promoter. After the obtained transformants were cultured for the time shown in FIG. 6, culture solutions (including yeast cells) were used for enzyme source. Using 5 mM 4-MU-alpha-galactopyranoside as a substrate, it was reacted at 37 degrees C. for 30 min. And the reaction was terminated by adding 200 micro litter of reaction stop solution (0.2 M glycine buffer (pH10.7)). Using a microplate reader for fluorescence (manufactured by Corona co. Ltd. MTP-32, Ex: 365 nm, Em: 450 nm), fluorescence was measured. Enzyme activity is represented by the hydrolyzed substrate per 1 mg of protein within 1 hour as micro mol (vertical line of FIG. 6). The results are shown in FIG. 6. FIG. 6 is a graph as an alternative of a figure showing assay results of alpha-galactosidase activity. From FIG. 6, although TIY20 strain loses activity of alpha-galactosidase, it is understood that C3-20, C3-7-2 and C4-1 showed good alpha-galactosidase A activity and especially, C3-20 and C3-7-2 showed higher alpha-galactosidase activity than wild-type W303-1A.

Example 6

Construction of Plasmid pREP1cdc6-1 Inserted Mutated cdc6-DNA Fragment

As follows, plasmid pREP1cdc6-1 (see FIG. 7(*a*)) was constructed by cloning the DNA fragment of mutated cdc6 (cdc6-1) into BamHI-NotI site of multicopy expression vector pREP1 for forced expression in fission yeast.

Amino acid sequence of Cdc6 of fission yeast is shown in sequence number 7 and DNA sequence coding Cdc6 is shown in sequence number 8. cdc6-1 mutant gene obtained by this example is the one in which 898th to 906th base (GAT ATT GAA) in sequence number 8 is substituted by GCCG-GCGCT. That is, a mutation was introduced in which amino acid residue coded by 898th to 906th sequence has DIE substituted by AGA. Thus obtained amino acid sequence of cdc6-1 is shown in sequence number 9 and DNA sequence coding cdc6-1 is shown in sequence number 10. Specifically, mutated cdc6 gene fragment was amplified using genome DNA extracted from fission yeast wild-type strain, TN8 strain (h$^{90}$leu1-32) as a template by site—directed method using PCR. For PCR reaction, forward primer (sequence number 11): 5'-AGCTC<u>GGATCC</u> (BamHI) GATGACAGATAG-GTCTTCAAATGAGGGCGTC-3', reverse primer (sequence number 12): 5'-TCGAGGCGACCTGCG-CAAGCGCCGGCAAAGCTCATGAT-3', forward primer (sequence number 13): 5'-AGCTCAGGATCAT-GAGCTTTGCCGGCGCTTGCGCAGGTCGCA-3', reverse primer (sequence number 14): 5'-TCGAG<u>GCGGCCGC</u> (NotI) TCACCAGGACATTTCATCAAATCTTTTCA-3' were used. By reverse primer of sequence number 12 and forward primer of sequence number 13, replacement of bases from 898th to 906th described as above occurs. The both sides of the obtained amplified fragment were digested by restriction enzyme BamHI and NotI and cloned into BamHI-NotI site of pREP1 vector (thus obtained plasmid is designated as pREP1cdc6-1). This plasmid could express mutated cdc6 gene (cdc6-1) under nmt1 promoter.

Isolation of a Sugar Chain-Modified Thermotolerant Strain

Sugar chain-modified strain KT97 (h-leu1-32 ura4-D18 Δoch1::ura4+) of fission yeast (Schizosaccharomyces pombe) was transformed with the plasmid pREP1cdc6-1 obtained as above. KT97 (Yoko-o T et al., FEBS Letters 489, 75-80. (2001)) is disclosed in Japanese publication of patent application 2001-161376. That is, KT97 is a gene disruptant of fission yeast its OCH1 gene was disrupted. Obtained transformant (KT97<pREP1cdc6-1) was cultured for introducing more mutations, regulating the conditions to enable division as much as possible in synthetic medium for fission yeast EMM (3 g phthalic acid K+, 2.2 g $NA_2HPO_4$, 5 g $NH_4Cl_2.2H_2O$, 1 g KCl, 0.04 g $Na_2SO_4$, 1 mg pantothenic acid, 10 mg nicotinic acid, 10 mg myo-inositol, 1 mg biotin, 0.5 mg boric acid, 0.4 mg $MnSO_4$, 0.4 mg $ZnSO_4.7H_2O$, 0.2 mg $FeCl_2.6H_2O$, 40 mg molybdic acid, 0.1 mg Kl, 40 mg $CuSO_4.H_2O$ 1 mg Citric acid/IL)(liquid). To obtain thermotolerant strain, these transformants were cultured on EMM solid medium at 37 degrees C. for 6 days and appearing colonies were picked up.

Example 7

Analysis of Sugar Chain Length Added to Yeast Invertase Protein

To measure length of N-linked sugar chain of 4 strains (C2-1, C2-2, C2-3 and C2-11) obtained in example 6, length of N-linked sugar chain which is added to yeast acid phosphatase produced in yeast was measured using following method. After each strain was cultured in 5 ml of YEA medium (30 g glucose, 5 g Yeast extract, 20 g agarose, 0.6 g adenine-$SO_4$, 0.05 g Uracil), it was cultured overnight in 5 ml low phosphate YPD medium.(10 g Yeast extract, 20 g Bacto Peptone, 10 mM $MgSO_4$, 20 g glucose/IL) and yeast cells were collected. To collected yeast cells, lysis buffer (62.5 mM Tris-HCl (pH6.8), 1 mM EDTA, 10% glycerol, 0.1 mM DTT, 2 mM PMSF) and glass beads were added to assume 20 OD/50 micro litter and were broken by vortex mixer at lowtemerature. After centrifugation of yeast lysate at 15000 rpm for 10 min, supernatant was recovered. To 25 micro litter of supernatant, 7 micro litter of sample buffer (62.5 mM Tris-HCl (pH6.8), 0.01% bromophenol blue, 15% glycerol) was added and each 10 micro litter thereof was electrophoresed (150V, 2 hours) using 4-20% gradient gel (upper layer buffer: 5.16 g Tris, 3.48 g glycine/IL; lower layer buffer: 14.5 g Tris, 0.024N HCl/IL). The gel was stirred in 100 mM sodium acetate (pH4.0) for 15 min, was transferred to color developing solution (100 mM Na-acetate (pH4.0), 24.6 mg 1-naftyl phosphate 1 sodium 1 hydrate, 16.7 mg o-dianisidine, Tetrazotized/50 ml) which is prewarmed to 37 degrees C. and was incubated at 37 degrees C. until color is developed. The result is shown in FIG. 8. FIG. 8 is a photo of SDS gel electrophoresis as an alternative of a figure for measurement of N-linked sugar chain length. Lanes of FIG. 8 show from left JY741 (wild-type), KT97 (parent strain) and C2-11. From FIG. 8, it is elucidated that N-linked sugar chain which is added to acid phosphatase produce by C2-11 strain obtained in example 6 has, as a parent strain KT97, shorter single sugar chain length compared to the wild-type strain (JY741). In addition, C2-11 strain was deposited to Patent Microorganisms Depositary. That is, by using C2-11 strain, a protein which has a desirable sugar chain can be obtained. That is, the present invention provides a method for producing a protein using C2-11 strain.

Analysis of Growth Recovery Rate

Next, a growth recovery rate was analyzed about the strain obtained in example 6. After culture in 5 ml YEA at 30 degrees C., yeast cells were transferred to 10 ml of YEA so as to adjust OD600 to 0.1 and were cultured at 30 degrees C. Yeast cells were collected at each timepoint and OD600 was measured. The result is shown in FIG. 9. FIG. 9 is a graph as an alternative of a figure showing growth recovery rate at 30 degrees C. From FIG. 9, it is understood that for all strains analyzed, growth rate exceeds that of KT97.

According to each of the above-mentioned examples, new mutant yeast strains of budding yeast and fission yeast which are excellent in thermotolerancy, growth activity and glycoprotein productivity can be obtained. As above, since an useful mutant yeast strain could be obtained by using a method of the present invention in budding yeast and fission yeast, the present invention need not be limited to budding yeast and fission yeast used in above examples but can be widely applied to the entire yeast and in every case, a new mutant strain of yeast can be obtained which is excellent in thermotolerance, growth activity and productivity of glycoprotein.

Analysis of Monosaccharide in Cell Wall of Yeast

Yeasts C4-1 and C3-7-2 obtained by example 1 were cultured by infiltration in 5 ml YPD at 30 degrees C. for 15 hours, yeast cells were collected by centrifugation (4000 rpm for 5 minutes) and then suspended in 1 ml of 10 mM Tris-HCl buffer (pH 7.5, 1 mM PMSF) and yeast cells were collected by centrifugation (4000 rpm for 5 minutes). This operation was performed three times to wash the yeast cells. The yeast cells were resuspended in the above-mentioned Tris-HCl buffer 0.1 ml, glass beads were added until the liquid level is reached and preserved at −20 degrees C. for 1 hour. After braking yeast cells with a voltex mixer, only cell lysate was collected and pellets were collected by centrifugation (1000 g, 10 minutes). Pellets (cell walls) were suspended in 1 ml of 1M NaCl and centrifuged, This operation was repeated three times to wash the pellets. Thereafter, the pellets were washed with 1 ml of 1 mM PMSF. The pellets were resuspended in 0.2 ml of 1 mM PMSF.

50 micro litter of sterilized ultrapure water was added to 50 micro litter of cell wall suspension, 100 micro litter of 4M TFA was added thereto, and then incubated at 100 degrees C. for 4 hours. After completely evaporating the solvent in a reduced-pressure dryer, 100 micro litter of 0.2 M ammonium acetate and 10 micro litter of acetic acid were added and incubated at room temperature for 30 minutes. After drying in a reduced-pressure dryer, 100 micro litter of 0.2 M ammonium acetate and 10 micro litter of acetic acid were added and incubated at room temperature for 30 minutes. Suspension was moved to a PA tube and dried. PA labeling was performed by using a PA labeling kit (PALSTATION Pyridylamination Reagent Kit for monosaccharide analysis (TaKaRa)). HPLC was performed with column: TSK-GEL SUGAR AX type (TOSHO), solvent: 0.7M potassium borate (pH9.0); acetonitrile=9:1, 65 degrees C., flow rate: 0.3 ml/min. Relative proportion of monosaccharide was calculated from a peak area ratio (FIG. 10). FIG. 10 is a graph as an alternative of a figure showing an analysis result of rate of content of monosaccharide in yeast cell wall. The vertical line indicates the percentage, GlcNAc represents N-acetylglucosamine, Glc represents glucose and Man represents mannose.

As shown in FIG. 10, while percentage of glucose in TIY20 strain was high as approximately 80% compared to percentage of glucose (approximately 45%) in WT, C4-1 strain and C3-7-2 strain that are the yeasts of the present invention showed further higher percentage of glucose (more than 90%). While breeding of yeast having high rate of content of beta-glucan such that percentage of glucose exceeds approximately 80% has been deemed technically very difficult, the yeast of the present invention has increased the percentage of glucose by more than approximately 10%. It can be said that the yeast of the present invention is extremely useful in the beta-glucan production technology using yeast from the perspectives of productivity, cost and the like, Yeast avoiding high temperature sensitivity or recovering growth activity and breeding method thereof of the present invention provides yeast which is excellent in thermotolerance, growth activity and productivity of glycoprotein and can be widely applied not only to budding yeast and fission yeast but also to yeast in general. Yeast which produces beta-glucan efficiently and breeding method thereof of the present invention provides yeast which is further excellent in producing beta-glucan compared to the conventionally known yeast, and can be widely applied not only to budding yeast and fission yeast but also to yeast in general. The present invention can be utilized in medical industry because effective use for production of glycoprotein and beta-glucan using yeast is enabled. Also, the present invention can be utilized for reagent industry because an appropriate control for specifying a gene-disruptant is enabled.

FIG. 1 is a figure of plasmid pAB100 and for confirm a restoration of thermotolerance in strains transformed with plasmid pAB100.

FIG. 7 is a figure of plasmid pREP1cdc6-1 and a figure for confirm a restoration of growth activity of the strain transformed with the plasmid pREP1cdc6-1.

SEQUENCE LISTING

Figures 1A, 1B, 1C:
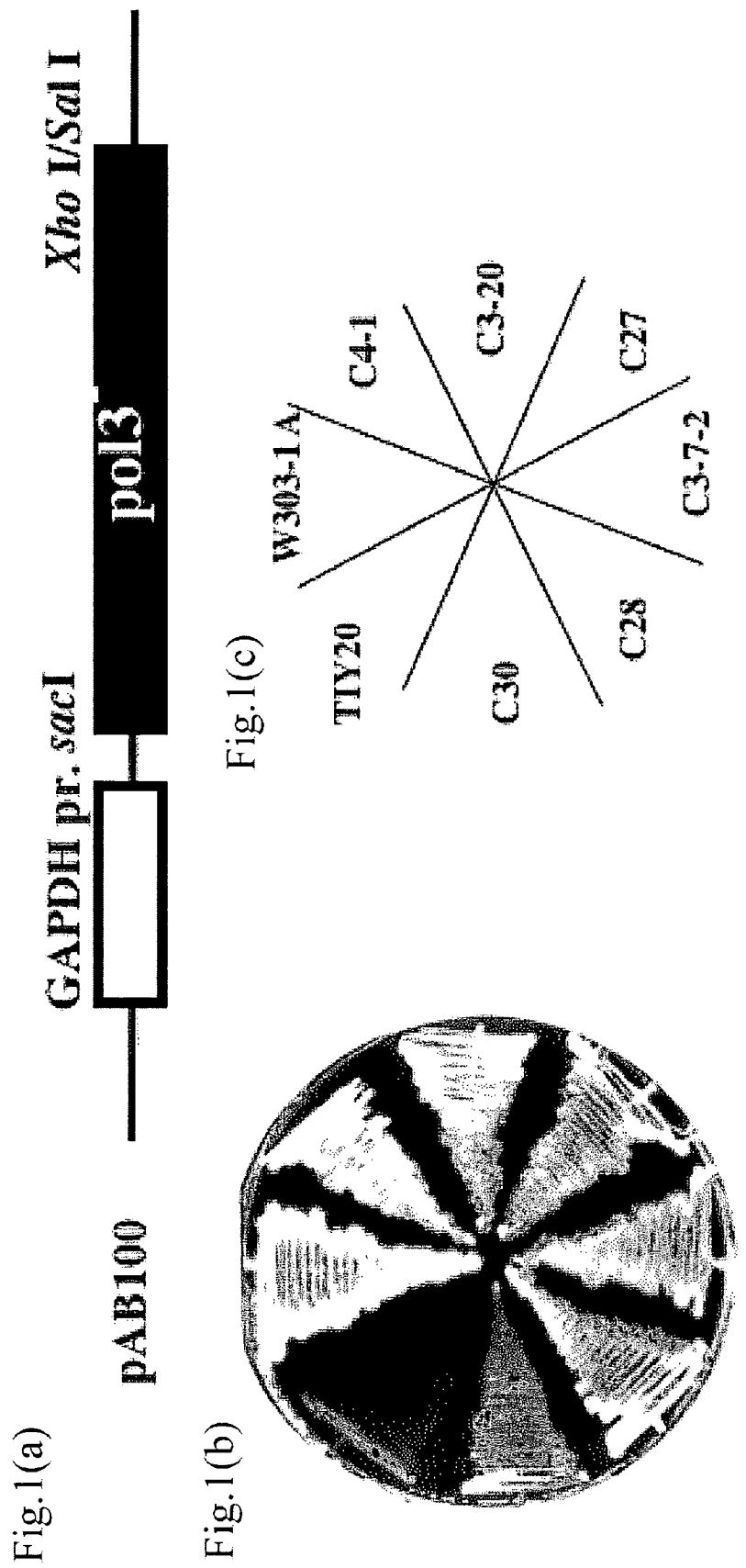
FIG. 1(a) is a Figure showing an outline of plasmid pAB100 and FIG. 1(b) is a photo as an alternative of a figure and FIG. 1(c) shows a fraction of FIG. 1(b).
Figure 2:
FIG. 2 is a photo of SDS gel electrophoresis as an alternative of a figure for measurement of N-linked sugar chain length.
Figure 3:
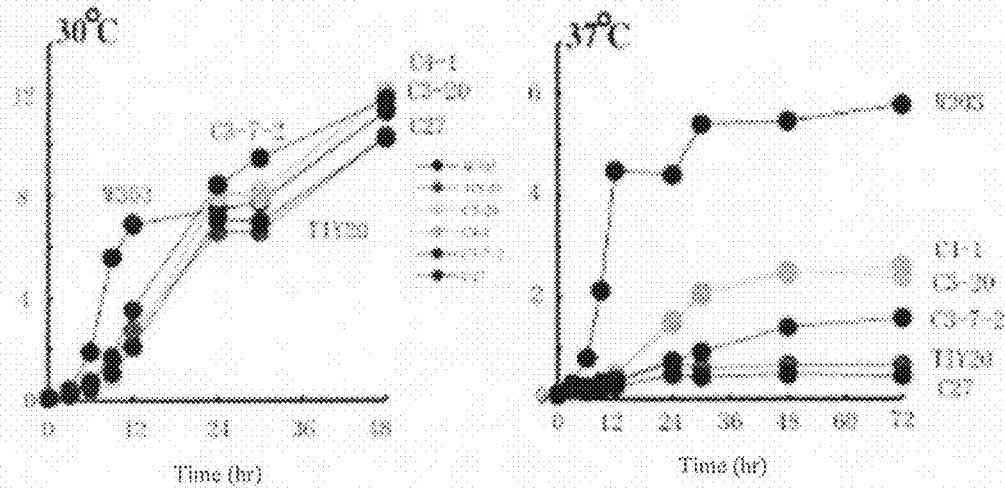
FIG. 3 is a graph as an alternative of a figure showing restoration rate of growth at 30 degrees C.
Figure 4:
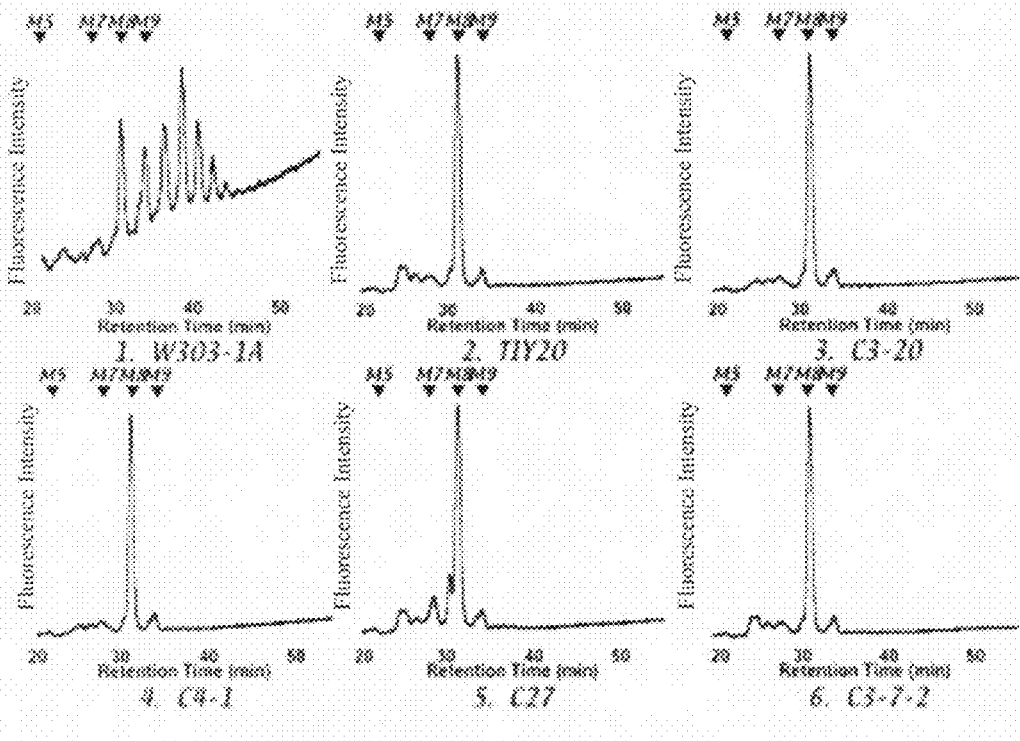
FIG. 4 is a graph as an alternative of a figure showing a result of column analysis for analysis of sugar chain structure.
Figure 5:
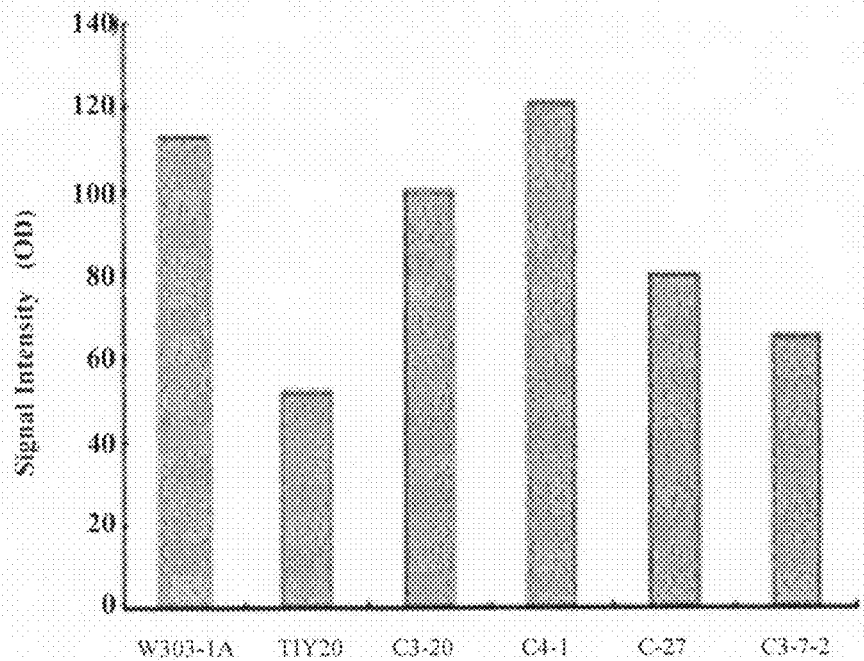
FIG. 5 is a graph as an alternative of a figure showing secretion efficiency of a protein from mutant strains.
Figure 6:
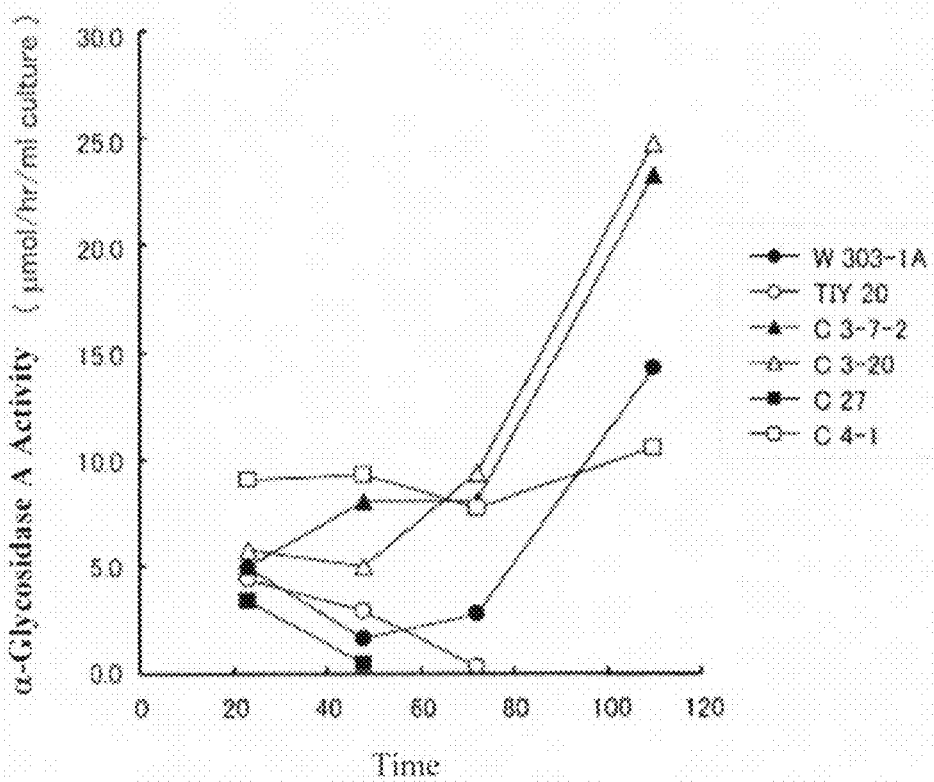
FIG. 6 is a graph as an alternative of a figure showing a result of assay for alpha-galactosidase A activity.
Figure 7A:
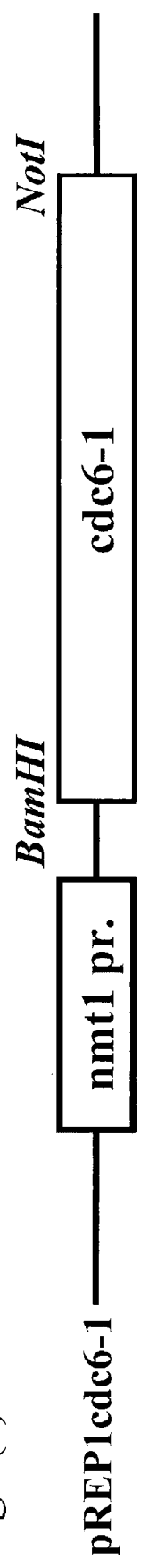
FIG. 7(a) is a figure showing an outline of plasmid pREPcdc6-1.
Figure 7C:
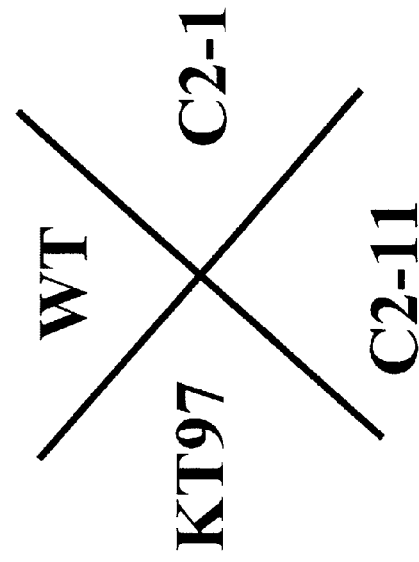
FIG. 7(b) is a photo as an alternative of a figure showing recovery of thermotolerance of a strain and FIG. 7(c) is a figure of a fractionation of FIG. 7(b).
Figure 7B:
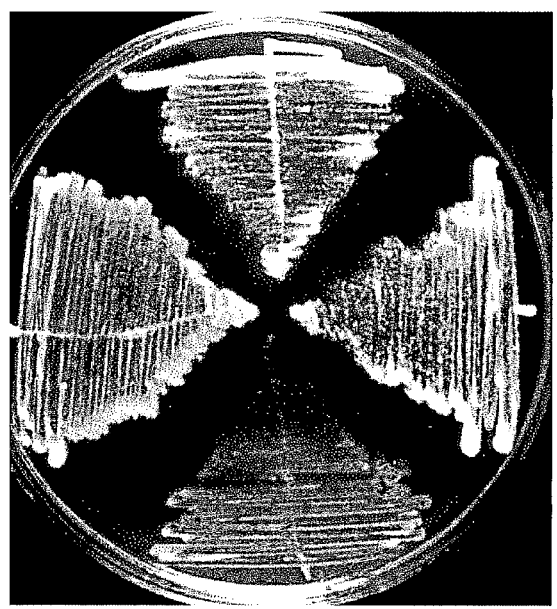
Figure 8:
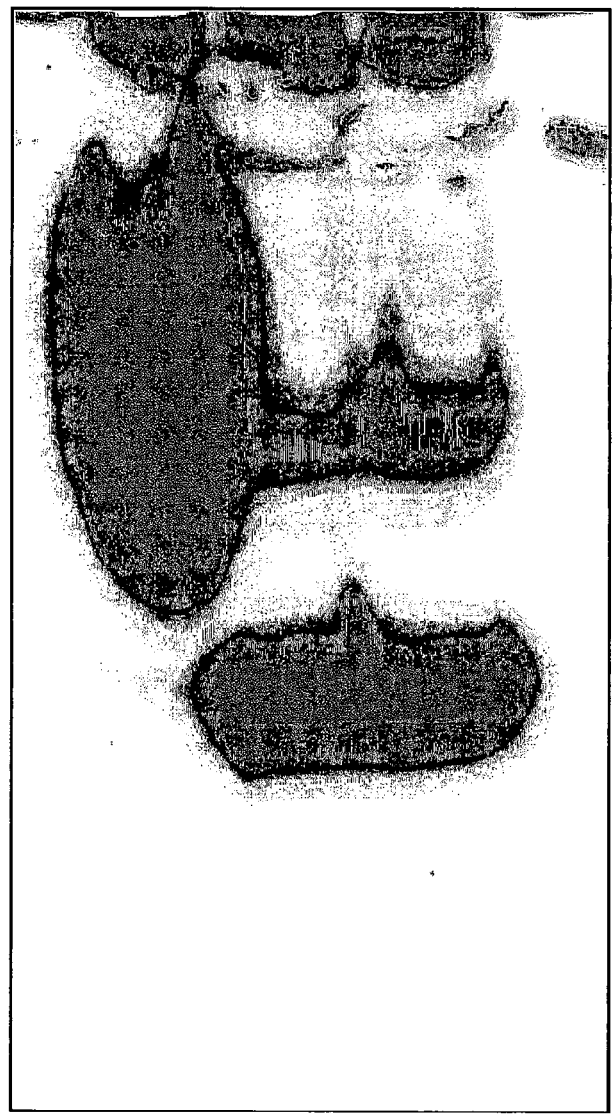
FIG. 8 is a photo of SDS gel electrophoresis as an alternative of a figure for measurement of N-linked sugar chain length.
Figure 9:
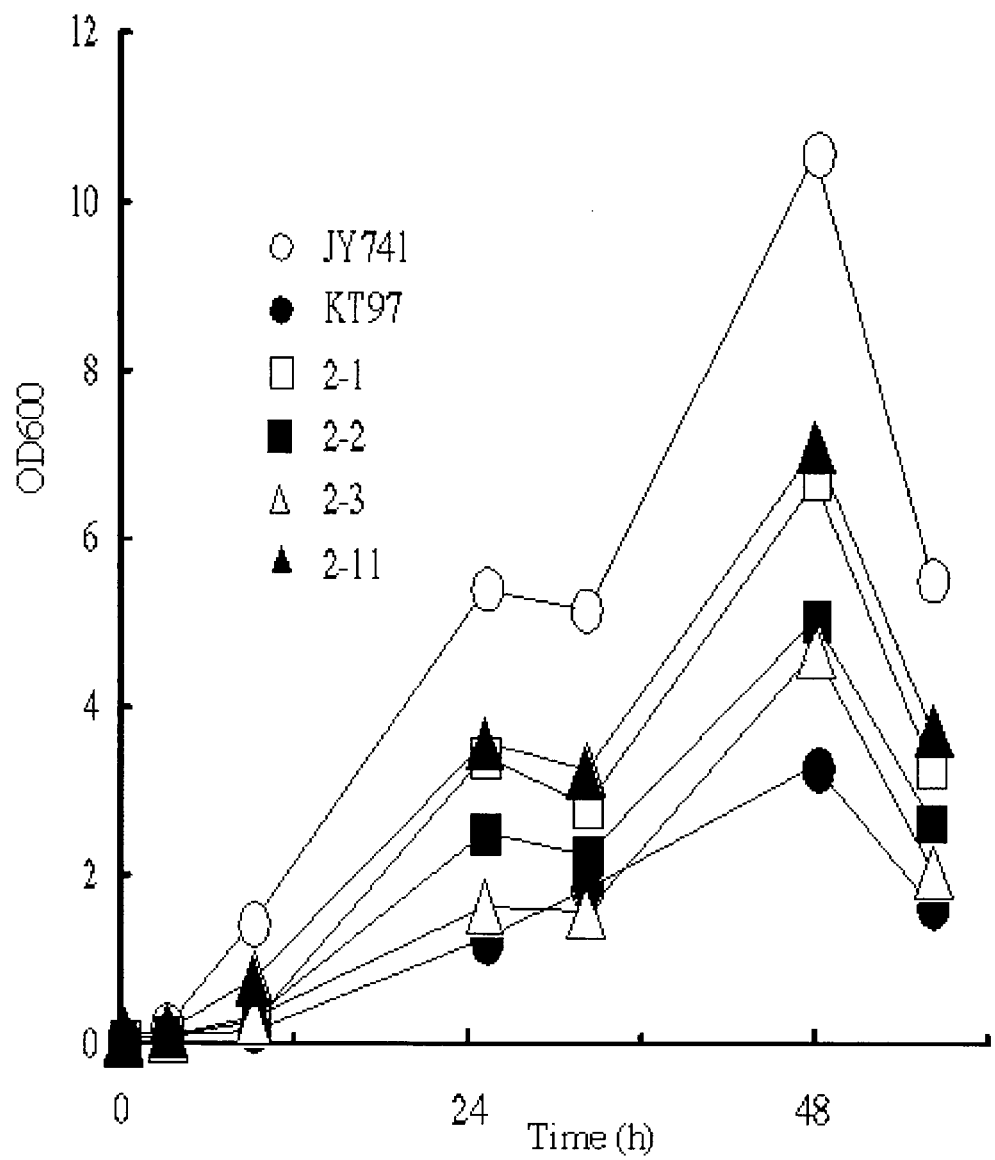
FIG. 9 is a graph as an alternative of a figure showing recovery rate of growth at 30 degrees C. in example 7.
Figure 10:
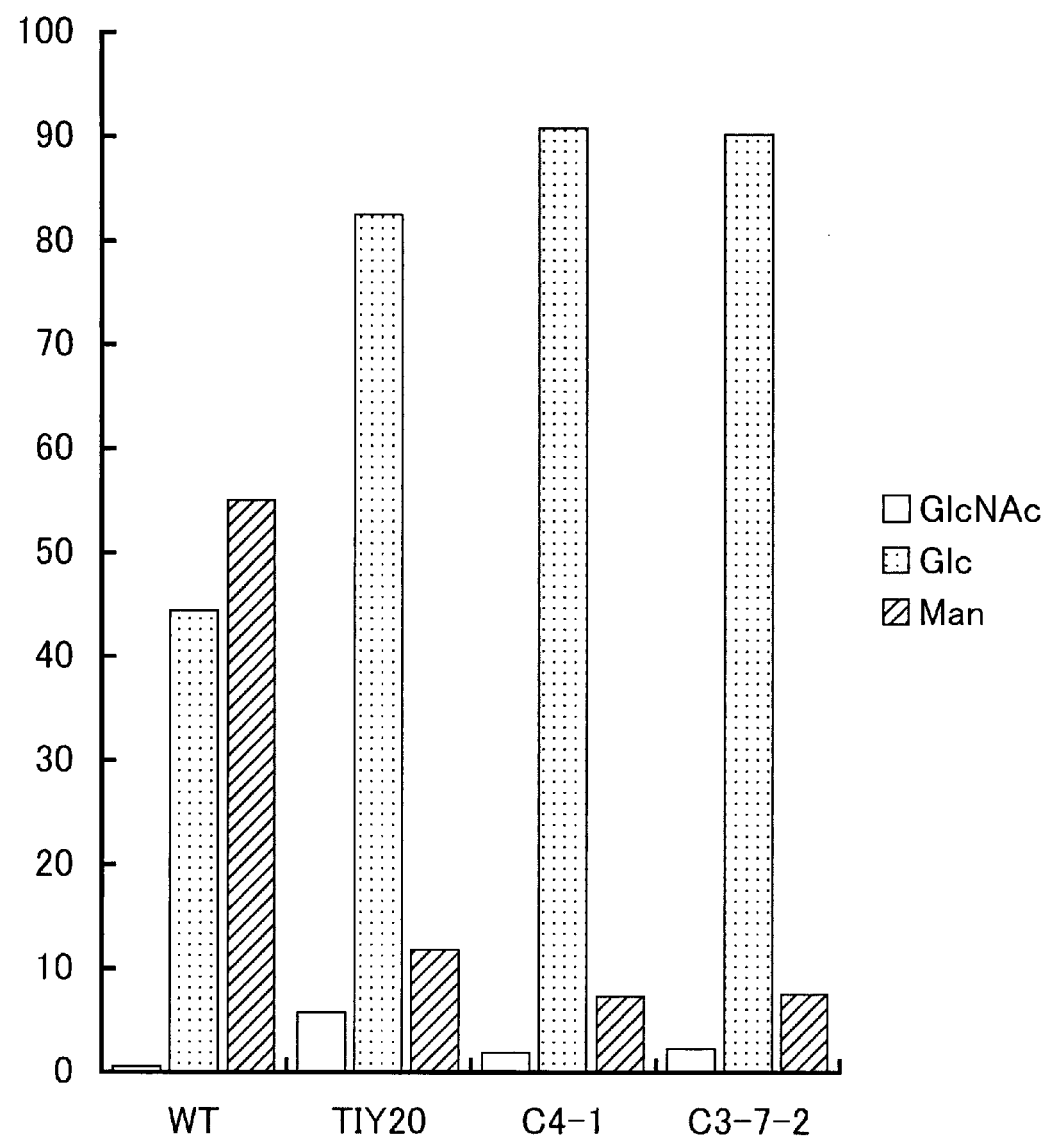
FIG. 10 shows a graph illustrating analysis results of contents of monosaccharides in yeast cell walls.

```
<160> NUMBER OF SEQ ID NOS: 14

<210> SEQ ID NO 1
<211> LENGTH: 1097
<212> TYPE: PRT
<213> ORGANISM: Saccharomyces cerevisiae

<400> SEQUENCE: 1

Met Ser Glu Lys Arg Ser Leu Pro Met Val Asp Val Lys Ile Asp Asp
1               5                   10                  15

Glu Asp Thr Pro Gln Leu Glu Lys Lys Ile Lys Arg Gln Ser Ile Asp
            20                  25                  30

His Gly Val Gly Ser Glu Pro Val Ser Thr Ile Glu Ile Ile Pro Ser
        35                  40                  45

Asp Ser Phe Arg Lys Tyr Asn Ser Gln Gly Phe Lys Ala Lys Asp Thr
    50                  55                  60

Asp Leu Met Gly Thr Gln Leu Glu Ser Thr Phe Glu Gln Asp Val Ser
65                  70                  75                  80

Gln Met Glu His Asp Met Ala Asp Gln Glu Glu His Asp Leu Ser Ser
                85                  90                  95

Phe Glu Arg Lys Lys Leu Pro Thr Asp Phe Asp Pro Ser Leu Tyr Asp
            100                 105                 110

Ile Ser Phe Gln Gln Ile Asp Ala Glu Gln Ser Val Leu Asn Gly Ile
        115                 120                 125

Lys Asp Glu Asn Thr Ser Thr Val Val Arg Phe Phe Gly Val Thr Ser
    130                 135                 140

Glu Gly His Ser Val Leu Cys Asn Val Thr Gly Phe Lys Asn Tyr Leu
145                 150                 155                 160
```

-continued

```
Tyr Val Pro Ala Pro Asn Ser Ser Asp Ala Asn Asp Gln Glu Gln Ile
            165                 170                 175

Asn Lys Phe Val His Tyr Leu Asn Glu Thr Phe Asp His Ala Ile Asp
            180                 185                 190

Ser Ile Glu Val Val Ser Lys Gln Ser Ile Trp Gly Tyr Ser Gly Asp
            195                 200                 205

Thr Lys Leu Pro Phe Trp Lys Ile Tyr Val Thr Tyr Pro His Met Val
            210                 215                 220

Asn Lys Leu Arg Thr Ala Phe Glu Arg Gly His Leu Ser Phe Asn Ser
225                 230                 235                 240

Trp Phe Ser Asn Gly Thr Thr Thr Tyr Asp Asn Ile Ala Tyr Thr Leu
                245                 250                 255

Arg Leu Met Val Asp Cys Gly Ile Val Gly Met Ser Trp Ile Thr Leu
                260                 265                 270

Pro Lys Gly Lys Tyr Ser Met Ile Glu Pro Asn Asn Arg Val Ser Ser
                275                 280                 285

Cys Gln Leu Glu Val Ser Ile Asn Tyr Arg Asn Leu Ile Ala His Pro
                290                 295                 300

Ala Glu Gly Asp Trp Ser His Thr Ala Pro Leu Arg Ile Met Ser Phe
305                 310                 315                 320

Asp Ile Glu Cys Ala Gly Arg Ile Gly Val Phe Pro Glu Pro Glu Tyr
                325                 330                 335

Asp Pro Val Ile Gln Ile Ala Asn Val Val Ser Ile Ala Gly Ala Lys
                340                 345                 350

Lys Pro Phe Ile Arg Asn Val Phe Thr Leu Asn Thr Cys Ser Pro Ile
                355                 360                 365

Thr Gly Ser Met Ile Phe Ser His Ala Thr Glu Glu Met Leu Ser
                370                 375                 380

Asn Trp Arg Asn Phe Ile Ile Lys Val Asp Pro Asp Val Ile Ile Gly
385                 390                 395                 400

Tyr Asn Thr Thr Asn Phe Asp Ile Pro Tyr Leu Leu Asn Arg Ala Lys
                405                 410                 415

Ala Leu Lys Val Asn Asp Phe Pro Tyr Phe Gly Arg Leu Lys Thr Val
                420                 425                 430

Lys Gln Glu Ile Lys Glu Ser Val Phe Ser Ser Lys Ala Tyr Gly Thr
                435                 440                 445

Arg Glu Thr Lys Asn Val Asn Ile Asp Gly Arg Leu Gln Leu Asp Leu
                450                 455                 460

Leu Gln Phe Ile Gln Arg Glu Tyr Lys Leu Arg Ser Tyr Thr Leu Asn
465                 470                 475                 480

Ala Val Ser Ala His Phe Leu Gly Glu Gln Lys Glu Asp Val His Tyr
                485                 490                 495

Ser Ile Ile Ser Asp Leu Gln Asn Gly Asp Ser Glu Thr Arg Arg
                500                 505                 510

Leu Ala Val Tyr Cys Leu Lys Asp Ala Tyr Leu Pro Leu Arg Leu Met
                515                 520                 525

Glu Lys Leu Met Ala Leu Val Asn Tyr Thr Glu Met Ala Arg Val Thr
530                 535                 540

Gly Val Pro Phe Ser Tyr Leu Leu Ala Arg Gly Gln Gln Ile Lys Val
545                 550                 555                 560

Val Ser Gln Leu Phe Arg Lys Cys Leu Glu Ile Asp Thr Val Ile Pro
                565                 570                 575
```

-continued

```
Asn Met Gln Ser Gln Ala Ser Asp Asp Gln Tyr Glu Gly Ala Thr Val
            580                 585                 590

Ile Glu Pro Ile Arg Gly Tyr Tyr Asp Val Pro Ile Ala Thr Leu Asp
        595                 600                 605

Phe Asn Ser Leu Tyr Pro Ser Ile Met Met Ala His Asn Leu Cys Tyr
    610                 615                 620

Thr Thr Leu Cys Asn Lys Ala Thr Val Glu Arg Leu Asn Leu Lys Ile
625                 630                 635                 640

Asp Glu Asp Tyr Val Ile Thr Pro Asn Gly Asp Tyr Phe Val Thr Thr
                645                 650                 655

Lys Arg Arg Arg Gly Ile Leu Pro Ile Ile Leu Asp Glu Leu Ile Ser
                660                 665                 670

Ala Arg Lys Arg Ala Lys Lys Asp Leu Arg Asp Glu Lys Asp Pro Phe
                675                 680                 685

Lys Arg Asp Val Leu Asn Gly Arg Gln Leu Ala Leu Lys Ile Ser Ala
        690                 695                 700

Asn Ser Val Tyr Gly Phe Thr Gly Ala Thr Val Gly Lys Leu Pro Cys
705                 710                 715                 720

Leu Ala Ile Ser Ser Val Thr Ala Tyr Gly Arg Thr Met Ile Leu
                725                 730                 735

Lys Thr Lys Thr Ala Val Gln Glu Lys Tyr Cys Ile Lys Asn Gly Tyr
            740                 745                 750

Lys His Asp Ala Val Val Val Tyr Gly Asp Thr Asp Ser Val Met Val
        755                 760                 765

Lys Phe Gly Thr Thr Asp Leu Lys Glu Ala Met Asp Leu Gly Thr Glu
        770                 775                 780

Ala Ala Lys Tyr Val Ser Thr Leu Phe Lys His Pro Ile Asn Leu Glu
785                 790                 795                 800

Phe Glu Lys Ala Tyr Phe Pro Tyr Leu Leu Ile Asn Lys Lys Arg Tyr
                805                 810                 815

Ala Gly Leu Phe Trp Thr Asn Pro Asp Lys Phe Asp Lys Leu Asp Gln
                820                 825                 830

Lys Gly Leu Ala Ser Val Arg Arg Asp Ser Cys Ser Leu Val Ser Ile
                835                 840                 845

Val Met Asn Lys Val Leu Lys Lys Ile Leu Ile Glu Arg Asn Val Asp
850                 855                 860

Gly Ala Leu Ala Phe Val Arg Glu Thr Ile Asn Asp Ile Leu His Asn
865                 870                 875                 880

Arg Val Asp Ile Ser Lys Leu Ile Ile Ser Lys Thr Leu Ala Pro Asn
                885                 890                 895

Tyr Thr Asn Pro Gln Pro His Ala Val Leu Ala Glu Arg Met Lys Arg
                900                 905                 910

Arg Glu Gly Val Gly Pro Asn Val Gly Asp Arg Val Asp Tyr Val Ile
            915                 920                 925

Ile Gly Gly Asn Asp Lys Leu Tyr Asn Arg Ala Glu Asp Pro Leu Phe
        930                 935                 940

Val Leu Glu Asn Asn Ile Gln Val Asp Ser Arg Tyr Tyr Leu Thr Asn
945                 950                 955                 960

Gln Leu Gln Asn Pro Ile Ile Ser Ile Val Ala Pro Ile Ile Gly Asp
                965                 970                 975

Lys Gln Ala Asn Gly Met Phe Val Val Lys Ser Ile Lys Ile Asn Thr
                980                 985                 990
```

```
Gly Ser Gln Lys Gly Gly Leu Met Ser Phe Ile Lys Lys Val Glu Ala
            995                 1000                1005

Cys Lys Ser Cys Lys Gly Pro Leu Arg Lys Gly Glu Gly Pro Leu
        1010                1015                1020

Cys Ser Asn Cys Leu Ala Arg Ser Gly Glu Leu Tyr Ile Lys Ala
        1025                1030                1035

Leu Tyr Asp Val Arg Asp Leu Glu Glu Lys Tyr Ser Arg Leu Trp
        1040                1045                1050

Thr Gln Cys Gln Arg Cys Ala Gly Asn Leu His Ser Glu Val Leu
        1055                1060                1065

Cys Ser Asn Lys Asn Cys Asp Ile Phe Tyr Met Arg Val Lys Val
        1070                1075                1080

Lys Lys Glu Leu Gln Glu Lys Val Glu Gln Leu Ser Lys Trp
        1085                1090                1095

<210> SEQ ID NO 2
<211> LENGTH: 3294
<212> TYPE: DNA
<213> ORGANISM: Saccharomyces cerevisiae

<400> SEQUENCE: 2
atgagtgaaa aaagatccct tcccatggtt gatgtgaaga tcgatgacga ggatactccc      60
cagttggaaa agaaaatcaa acggcaatca atagatcatg gtgttggaag tgaacctgtt     120
tcaacaatag agattattcc gagtgattct tttcgaaaat ataatagtca aggcttcaaa     180
gcaaaggata cagatttaat gggtacgcaa ttagagtcta cttttgaaca agacgtatcg     240
caaatggaac atgatatggc cgaccaagaa gagcatgacc tgtcatcatt cgagcgtaag     300
aaacttccaa ccgattttga cccaagtttg tatgatattt cttccaaca aattgatgcg     360 gaacagagcg tactgaatgg tatcaaagat gaaaatacat ctaccgtggt aaggtttttt     420
ggtgtcacta gtgaaggaca ctctgtactt tgtaatgtta cagggttcaa gaactatctt     480
tacgtcccag cgcccaattc ttccgacgct aacgatcagg agcaaatcaa caagtttgtg     540
cactatttaa acgaaacatt tgaccacgct attgattcga ttgaagttgt atctaaacag     600
tctatctggg gttattccgg agataccaaa ttaccattct ggaaaatata cgtcacctat     660
ccgcatatgg tcaacaaact gcgtactgcg tttgaaagag gtcatctttc attcaactcg     720
tggttttcta acggcacgac tacttatgat aacattgcct acactttaag gttaatggta     780
gattgtggaa ttgtcggtat gtcctggata acattaccaa aggaaagta ttcgatgatt     840 gagcctaata acagagtttc ctcttgtcag ttggaagttt caattaatta tcgtaaccta     900
atagcacatc ctgctgaggg tgattggtct catacagctc cattgcgtat catgtccttt     960
gatatcgagt gtgctggtag gattggcgtc tttccggaac tgaatacga tcccgtcatc    1020 caaattgcca acgttgtgag tattgctggc gctaagaaac cattcattcg taatgtgttt    1080
actctgaata catgctcacc cataacaggt tcaatgattt tttcccacgc cactgaagag    1140
gaaatgttga gcaattggcg taactttatc atcaaagttg atcctgatgt tatcattggt    1200
tataatacta caaattttga tatcccttat cttttaaacc gtgcaaaggc gctaaaggtg    1260
aatgatttcc catattttgg aaggttaaaa accgttaagc aagaaattaa agagtctgtg    1320
ttctcttcga aggcttatgg tacaagagaa accaaaaatg tcaatattga cggccgatta    1380
cagttggatc ttttgcaatt tattcagcgt gagtataaac taagatccta cacgttgaat    1440
gcagtctctg cgcactttt aggtgaacag aaggaggatg tacattatag catcatttct    1500
```

-continued

```
gatctacaaa atggcgatag tgaaacaaga agaaggttgg ccgtttactg tttgaaagac    1560
gcctacctgc ctttaaggct tatggaaaaa ctaatggcgt tagttaacta tacagaaatg    1620
gctcgtgtta caggtgtgcc attttcatat ttactagctc gtggtcaaca aattaaagtt    1680
gtttctcaac tatttcgaaa gtgcctggag attgatactg tgatacctaa catgcaatct    1740
caggcctctg atgaccaata tgagggtgcc actgttattg agccatattcg tggttattac    1800 gatgtaccga ttgcaacttt ggatttcaat tctttatatc caagtattat gatggcgcac    1860
aacctatgtt atacaacact tgtaacaaa gctactgtag agagattgaa tcttaaaatt    1920
gacgaagact acgtcataac acctaatgga gattattttg ttaccacaaa agaaggcgt    1980 ggtatattac caattattct ggatgaatta ataagtgcta gaaaacgcgc taaaaaagat    2040
ctgagagatg agaaggatcc attcaaaaga gatgttttaa atggtagaca attggctttg    2100
aagatttcag ctaactctgt ctatggtttt acaggagcga cggtgggtaa attgccatgt    2160
ttagccattt cttcatctgt tactgcttat ggtcgtacca tgattttaaa aactaaaacc    2220
gcagtccaag aaaaatattg tataaagaat ggttataagc acgatgccgt tgtggtttac    2280
ggtgacactg attccgttat ggtaaagttt ggtacaacag atttaaagga agctatggat    2340
cttggtaccg aagctgccaa atatgtctcc actctattca acatccgat taacttagaa    2400 tttgaaaaag catacttccc ttaccttttg ataaataaaa agcgttatgc aggtttattc    2460
tggactaatc ctgacaagtt tgacaagttg gaccaaaaag gccttgcttc tgtccgtcgt    2520
gattcctgtt ccttggtttc tattgttatg aataaagttt taagaaaat tttaattgaa    2580 agaaatgtag atggtgcttt agcttttgtc agagaaacta tcaatgatat tctgcataat    2640
agagtagata tttcaaagtt gattatatca aagacgttag ccccaaatta cacaaatcca    2700
cagccgcacg ccgttttggc tgaacgtatg aagaggagag agggcgttgg tccaaatgtt    2760
ggtgatcgtg tggactatgt cattatcggt ggtaatgata aactttacaa tagagcagaa    2820
gatccattat ttgtactaga aaacaatatt caagtggatt cgcgctatta tttaactaat    2880
caattacaaa atccaatcat tagtattgtt gcacctatta ttggcgacaa acaggcgaac    2940
ggtatgttcg ttgtgaaatc cattaaaatt aacacaggct ctcaaaaagg aggcttgatg    3000
agctttatta aaaagttga ggcttgtaaa agttgtaaag gtccgttgag gaaaggtgaa    3060
ggccctcttt gttcaaactg tctagcaagg tctggagaat tatacataaa ggcattatac    3120
gatgtcagag atttagagga aaaatactca agattatgga cacaatgcca aaggtgcgct    3180
ggtaacttac atagtgaagt tttgtgttca aataagaact gtgacatttt ttatatgcgg    3240
gttaaggtta aaaagagct gcaggagaaa gtagaacaat taagcaaatg gtaa          3294
```

<210> SEQ ID NO 3
<211> LENGTH: 1097
<212> TYPE: PRT
<213> ORGANISM: Saccharomyces cerevisiae

<400> SEQUENCE: 3

```
Met Ser Glu Lys Arg Ser Leu Pro Met Val Asp Val Lys Ile Asp Asp
1               5                   10                  15

Glu Asp Thr Pro Gln Leu Glu Lys Lys Ile Lys Arg Gln Ser Ile Asp
            20                  25                  30

His Gly Val Gly Ser Glu Pro Val Ser Thr Ile Glu Ile Ile Pro Ser
        35                  40                  45

Asp Ser Phe Arg Lys Tyr Asn Ser Gln Gly Phe Lys Ala Lys Asp Thr
    50                  55                  60
```

-continued

```
Asp Leu Met Gly Thr Gln Leu Glu Ser Thr Phe Gln Asp Val Ser
 65                  70                  75                  80

Gln Met Glu His Asp Met Ala Asp Gln Glu His Asp Leu Ser Ser
             85                  90                  95

Phe Glu Arg Lys Lys Leu Pro Thr Asp Phe Asp Pro Ser Leu Tyr Asp
            100                 105                 110

Ile Ser Phe Gln Gln Ile Asp Ala Glu Gln Ser Val Leu Asn Gly Ile
            115                 120                 125

Lys Asp Glu Asn Thr Ser Thr Val Val Arg Phe Phe Gly Val Thr Ser
130                 135                 140

Glu Gly His Ser Val Leu Cys Asn Val Thr Gly Phe Lys Asn Tyr Leu
145                 150                 155                 160

Tyr Val Pro Ala Pro Asn Ser Ser Asp Ala Asn Asp Gln Glu Gln Ile
                165                 170                 175

Asn Lys Phe Val His Tyr Leu Asn Glu Thr Phe Asp His Ala Ile Asp
            180                 185                 190

Ser Ile Glu Val Val Ser Lys Gln Ser Ile Trp Gly Tyr Ser Gly Asp
            195                 200                 205

Thr Lys Leu Pro Phe Trp Lys Ile Tyr Val Thr Tyr Pro His Met Val
210                 215                 220

Asn Lys Leu Arg Thr Ala Phe Glu Arg Gly His Leu Ser Phe Asn Ser
225                 230                 235                 240

Trp Phe Ser Asn Gly Thr Thr Thr Tyr Asp Asn Ile Ala Tyr Thr Leu
                245                 250                 255

Arg Leu Met Val Asp Cys Gly Ile Val Gly Met Ser Trp Ile Thr Leu
                260                 265                 270

Pro Lys Gly Lys Tyr Ser Met Ile Glu Pro Asn Asn Arg Val Ser Ser
            275                 280                 285

Cys Gln Leu Glu Val Ser Ile Asn Tyr Arg Asn Leu Ile Ala His Pro
290                 295                 300

Ala Glu Gly Asp Trp Ser His Thr Ala Pro Leu Arg Ile Met Ser Phe
305                 310                 315                 320

Ala Ile Ala Cys Ala Gly Arg Ile Gly Val Phe Pro Glu Pro Glu Tyr
                325                 330                 335

Asp Pro Val Ile Gln Ile Ala Asn Val Val Ser Ile Ala Gly Ala Lys
            340                 345                 350

Lys Pro Phe Ile Arg Asn Val Phe Thr Leu Asn Thr Cys Ser Pro Ile
            355                 360                 365

Thr Gly Ser Met Ile Phe Ser His Ala Thr Glu Glu Glu Met Leu Ser
370                 375                 380

Asn Trp Arg Asn Phe Ile Ile Lys Val Asp Pro Asp Val Ile Ile Gly
385                 390                 395                 400

Tyr Asn Thr Thr Asn Phe Asp Ile Pro Tyr Leu Leu Asn Arg Ala Lys
                405                 410                 415

Ala Leu Lys Val Asn Asp Phe Pro Tyr Phe Gly Arg Leu Lys Thr Val
            420                 425                 430

Lys Gln Glu Ile Lys Glu Ser Val Phe Ser Ser Lys Ala Tyr Gly Thr
            435                 440                 445

Arg Glu Thr Lys Asn Val Asn Ile Asp Gly Arg Leu Gln Leu Asp Leu
        450                 455                 460

Leu Gln Phe Ile Gln Arg Glu Tyr Lys Leu Arg Ser Tyr Thr Leu Asn
465                 470                 475                 480
```

-continued

```
Ala Val Ser Ala His Phe Leu Gly Glu Gln Lys Glu Asp Val His Tyr
                485                 490                 495
Ser Ile Ile Ser Asp Leu Gln Asn Gly Asp Ser Glu Thr Arg Arg Arg
            500                 505                 510
Leu Ala Val Tyr Cys Leu Lys Asp Ala Tyr Leu Pro Leu Arg Leu Met
        515                 520                 525
Glu Lys Leu Met Ala Leu Val Asn Tyr Thr Glu Met Ala Arg Val Thr
    530                 535                 540
Gly Val Pro Phe Ser Tyr Leu Leu Ala Arg Gly Gln Gln Ile Lys Val
545                 550                 555                 560
Val Ser Gln Leu Phe Arg Lys Cys Leu Glu Ile Asp Thr Val Ile Pro
                565                 570                 575
Asn Met Gln Ser Gln Ala Ser Asp Asp Gln Tyr Glu Gly Ala Thr Val
            580                 585                 590
Ile Glu Pro Ile Arg Gly Tyr Tyr Asp Val Pro Ile Ala Thr Leu Asp
        595                 600                 605
Phe Asn Ser Leu Tyr Pro Ser Ile Met Met Ala His Asn Leu Cys Tyr
    610                 615                 620
Thr Thr Leu Cys Asn Lys Ala Thr Val Glu Arg Leu Asn Leu Lys Ile
625                 630                 635                 640
Asp Glu Asp Tyr Val Ile Thr Pro Asn Gly Asp Tyr Phe Val Thr Thr
                645                 650                 655
Lys Arg Arg Arg Gly Ile Leu Pro Ile Ile Leu Asp Glu Leu Ile Ser
            660                 665                 670
Ala Arg Lys Arg Ala Lys Lys Asp Leu Arg Asp Glu Lys Asp Pro Phe
        675                 680                 685
Lys Arg Asp Val Leu Asn Gly Arg Gln Leu Ala Leu Lys Ile Ser Ala
    690                 695                 700
Asn Ser Val Tyr Gly Phe Thr Gly Ala Thr Val Gly Lys Leu Pro Cys
705                 710                 715                 720
Leu Ala Ile Ser Ser Ser Val Thr Ala Tyr Gly Arg Thr Met Ile Leu
                725                 730                 735
Lys Thr Lys Thr Ala Val Gln Glu Lys Tyr Cys Ile Lys Asn Gly Tyr
            740                 745                 750
Lys His Asp Ala Val Val Val Tyr Gly Asp Thr Asp Ser Val Met Val
        755                 760                 765
Lys Phe Gly Thr Thr Asp Leu Lys Glu Ala Met Asp Leu Gly Thr Glu
    770                 775                 780
Ala Ala Lys Tyr Val Ser Thr Leu Phe Lys His Pro Ile Asn Leu Glu
785                 790                 795                 800
Phe Glu Lys Ala Tyr Phe Pro Tyr Leu Leu Ile Asn Lys Lys Arg Tyr
                805                 810                 815
Ala Gly Leu Phe Trp Thr Asn Pro Asp Lys Phe Asp Lys Leu Asp Gln
            820                 825                 830
Lys Gly Leu Ala Ser Val Arg Arg Asp Ser Cys Ser Leu Val Ser Ile
        835                 840                 845
Val Met Asn Lys Val Leu Lys Lys Ile Leu Ile Glu Arg Asn Val Asp
    850                 855                 860
Gly Ala Leu Ala Phe Val Arg Glu Thr Ile Asn Asp Ile Leu His Asn
865                 870                 875                 880
Arg Val Asp Ile Ser Lys Leu Ile Ile Ser Lys Thr Leu Ala Pro Asn
                885                 890                 895
```

-continued

```
Tyr Thr Asn Pro Gln Pro His Ala Val Leu Ala Glu Arg Met Lys Arg
            900                 905                 910
Arg Glu Gly Val Gly Pro Asn Val Gly Asp Arg Val Asp Tyr Val Ile
        915                 920                 925
Ile Gly Gly Asn Asp Lys Leu Tyr Asn Arg Ala Glu Asp Pro Leu Phe
    930                 935                 940
Val Leu Glu Asn Asn Ile Gln Val Asp Ser Arg Tyr Tyr Leu Thr Asn
945                 950                 955                 960
Gln Leu Gln Asn Pro Ile Ile Ser Ile Val Ala Pro Ile Ile Gly Asp
                965                 970                 975
Lys Gln Ala Asn Gly Met Phe Val Val Lys Ser Ile Lys Ile Asn Thr
            980                 985                 990
Gly Ser Gln Lys Gly Gly Leu Met Ser Phe Ile Lys Lys Val Glu Ala
        995                 1000                1005
Cys Lys Ser Cys Lys Gly Pro Leu Arg Lys Gly Glu Gly Pro Leu
    1010                1015                1020
Cys Ser Asn Cys Leu Ala Arg Ser Gly Glu Leu Tyr Ile Lys Ala
    1025                1030                1035
Leu Tyr Asp Val Arg Asp Leu Glu Glu Lys Tyr Ser Arg Leu Trp
    1040                1045                1050
Thr Gln Cys Gln Arg Cys Ala Gly Asn Leu His Ser Glu Val Leu
    1055                1060                1065
Cys Ser Asn Lys Asn Cys Asp Ile Phe Tyr Met Arg Val Lys Val
    1070                1075                1080
Lys Lys Glu Leu Gln Glu Lys Val Glu Gln Leu Ser Lys Trp
    1085                1090                1095
```

<210> SEQ ID NO 4
<211> LENGTH: 3294
<212> TYPE: DNA
<213> ORGANISM: Saccharomyces cerevisiae

<400> SEQUENCE: 4

| | | |
|---|---|---|
| atgagtgaaa aagatccct tcccatggtt gatgtgaaga tcgatgacga ggatactccc | 60 |
| cagttggaaa agaaaatcaa acggcaatca atagatcatg gtgttggaag tgaacctgtt | 120 |
| tcaacaatag agattattcc gagtgattct tttcgaaaat ataatagtca aggcttcaaa | 180 |
| gcaaaggata cagatttaat gggtacgcaa ttagagtcta cttttgaaca agacgtatcg | 240 |
| caaatggaac atgatatggc cgaccaagaa gagcatgacc tgtcatcatt cgagcgtaag | 300 |
| aaacttccaa ccgattttga cccaagtttg tatgatattt cttttccaaca aattgatgcg | 360 |
| gaacagagcg tactgaatgg tatcaaagat gaaaatacat ctaccgtggt aaggtttttt | 420 |
| ggtgtcacta gtgaaggaca ctctgtactt tgtaatgtta cagggttcaa gaactatctt | 480 |
| tacgtcccag cgcccaattc ttccgacgct aacgatcagg agcaaatcaa caagtttgtg | 540 |
| cactatttaa acgaaacatt tgaccacgct attgattcga ttgaagttgt atctaaacag | 600 |
| tctatctggg ttattccgg agataccaaa ttaccattct ggaaaatata cgtcacctat | 660 |
| ccgcatatgg tcaacaaact gcgtactgcg tttgaaagag gtcatctttc attcaactcg | 720 |
| tggttttcta acggcacgac tactatgat aacattgcct acactttaag gttaatggta | 780 |
| gattgtggaa ttgtcggtat gtcctggata acattaccaa aaggaaagta ttcgatgatt | 840 |
| gagcctaata cagagttttc ctcttgtcag ttggaagttt caattaatta tcgtaaccta | 900 |
| atagcacatc ctgctgaggg tgattggtct catacagctc cattgcgtat catgtccttt | 960 |

```
gctatcgcgt gtgctggtag gattggcgtc tttccggaac ctgaatacga tcccgtcatc    1020
caaattgcca acgttgtgag tattgctggc gctaagaaac cattcattcg taatgtgttt    1080
actctgaata catgctcacc cataacaggt tcaatgattt tttcccacgc cactgaagag    1140
gaaatgttga gcaattggcg taactttatc atcaaagttg atcctgatgt tatcattggt    1200
tataatacta caaattttga tatcccttat cttttaaacc gtgcaaaggc gctaaaggtg    1260
aatgatttcc catattttgg aaggttaaaa accgttaagc aagaaattaa agagtctgtg    1320
ttctcttcga aggcttatgg tacaagagaa accaaaaatg tcaatattga cggccgatta    1380
cagttggatc ttttgcaatt tattcagcgt gagtataaac taagatccta cacgttgaat    1440
gcagtctctg cgcactttt aggtgaacag aaggaggatg tacattatag catcatttct    1500
gatctacaaa atggcgatag tgaaacaaga agaaggttgg ccgtttactg tttgaaagac    1560
gcctacctgc ctttaaggct tatggaaaaa ctaatggcgt tagttaacta tacagaaatg    1620
gctcgtgtta caggtgtgcc attttcatat ttactagctc gtggtcaaca aattaaagtt    1680
gtttctcaac tatttcgaaa gtgcctggag attgatactg tgatacctaa catgcaatct    1740
caggcctctg atgaccaata tgagggtgcc actgttattg agcctattcg tggttattac    1800
gatgtaccga ttgcaacttt ggatttcaat tctttatatc caagtattat gatggcgcac    1860
aacctatgtt atacaacact tgtaacaaa gctactgtag agagattgaa tcttaaaatt    1920
gacgaagact acgtcataac acctaatgga gattattttg ttaccacaaa agaaggcgt    1980 ggtatattac caattattct ggatgaatta ataagtgcta aaaacgcgc taaaaaagat    2040 ctgagagatg agaaggatcc attcaaaaga gatgttttaa atggtagaca attggctttg    2100
aagatttcag ctaactctgt ctatggtttt acaggagcga cggtgggtaa attgccatgt    2160
ttagccattt cttcatctgt tactgcttat ggtcgtacca tgatttttaaa aactaaaacc    2220 gcagtccaag aaaaatattg tataaagaat ggttataagc acgatgccgt tgtggtttac    2280
ggtgacactg attccgttat ggtaaagttt ggtacaacag atttaaagga agctatggat    2340
cttggtaccg aagctgccaa atatgtctcc actctattca acatccgat taacttagaa    2400 tttgaaaaag catacttccc ttaccttttg ataaataaaa agcgttatgc aggtttattc    2460
tggactaatc ctgacaagtt tgacaagttg gaccaaaaag gccttgcttc tgtccgtcgt    2520
gattcctgtt ccttggtttc tattgttatg aataaagttt taaagaaaat tttaattgaa    2580
agaaatgtag atggtgcttt agcttttgtc agagaaacta tcaatgatat tctgcataat    2640
agagtagata tttcaaagtt gattatatca aagacgttag ccccaaatta cacaaatcca    2700
cagccgcacg ccgttttggc tgaacgtatg aagaggagag agggcgttgg tccaaatgtt    2760
ggtgatcgtg tggactatgt cattatcggt ggtaatgata aactttacaa tagagcagaa    2820
gatccattat ttgtactaga aaacaatatt caagtggatt cgcgctatta tttaactaat    2880
caattacaaa atccaatcat tagtattgtt gcacctatta ttggcgacaa acaggcgaac    2940
ggtatgttcg ttgtgaaatc cattaaaatt aacacaggct ctcaaaaagg aggcttgatg    3000
agctttatta aaaagttga ggcttgtaaa agttgtaaag gtccgttgag gaaggtgaa    3060 ggccctcttt gttcaaactg tctagcaagg tctggagaat tatacataaa ggcattatac    3120
gatgtcagag atttagagga aaaatactca agattatgga cacaatgcca aggtgcgct    3180 ggtaacttac atagtgaagt tttgtgttca aataagaact gtgacatttt ttatatgcgg    3240
gttaaggtta aaaagagct gcaggagaaa gtagaacaat taagcaaatg gtaa         3294
```

-continued

<210> SEQ ID NO 5
<211> LENGTH: 38
<212> TYPE: DNA
<213> ORGANISM: artificial sequence
<220> FEATURE:
<223> OTHER INFORMATION: primer

<400> SEQUENCE: 5
agctcgagct catgagtgaa aaaagatccc ttcccatg        38

<210> SEQ ID NO 6
<211> LENGTH: 37
<212> TYPE: DNA
<213> ORGANISM: artificial sequence
<220> FEATURE:
<223> OTHER INFORMATION: primer

<400> SEQUENCE: 6
gcatcgcggc cgcttaccat ttgcttaatt gttctac        37

<210> SEQ ID NO 7
<211> LENGTH: 1086
<212> TYPE: PRT
<213> ORGANISM: Schizosaccharomyces pombe

<400> SEQUENCE: 7

```
Met Thr Asp Arg Ser Ser Asn Glu Gly Val Val Leu Asn Lys Glu Asn
1               5                   10                  15

Tyr Pro Phe Pro Arg Arg Asn Gly Ser Ile His Gly Glu Ile Thr Asp
            20                  25                  30

Val Lys Arg Arg Arg Leu Ser Glu Arg Asn Gly Tyr Gly Asp Lys Lys
        35                  40                  45

Gly Ser Ser Ser Lys Glu Lys Thr Ser Ser Phe Glu Asp Glu Ser Ala
    50                  55                  60

Glu Tyr Ala Ser Gln Leu Asp Gln Asp Glu Ile Lys Ser Ser Lys Asp
65                  70                  75                  80

Gln Gln Trp Gln Arg Pro Ala Leu Pro Ala Ile Asn Pro Glu Lys Asp
                85                  90                  95

Asp Ile Tyr Phe Gln Gln Ile Asp Ser Glu Glu Phe Thr Glu Gly Ser
            100                 105                 110

Val Pro Ser Ile Arg Leu Phe Gly Val Thr Asp Asn Gly Asn Ser Ile
        115                 120                 125

Leu Val His Val Val Gly Phe Leu Pro Tyr Phe Tyr Val Lys Ala Pro
    130                 135                 140

Val Gly Phe Arg Pro Glu Met Leu Glu Arg Phe Thr Gln Asp Leu Asp
145                 150                 155                 160

Ala Thr Cys Asn Gly Gly Val Ile Asp His Cys Ile Ile Glu Met Lys
                165                 170                 175

Glu Asn Leu Tyr Gly Phe Gln Gly Asn Glu Lys Ser Pro Phe Ile Lys
            180                 185                 190

Ile Phe Thr Thr Asn Pro Arg Ile Leu Ser Arg Ala Arg Asn Val Phe
        195                 200                 205

Glu Arg Gly Glu Phe Asn Phe Glu Leu Phe Pro Val Gly Val Gly
    210                 215                 220

Val Thr Thr Phe Glu Ser Asn Thr Gln Tyr Leu Leu Arg Phe Met Ile
225                 230                 235                 240

Asp Cys Asp Val Val Gly Met Asn Trp Ile His Leu Pro Ala Ser Lys
                245                 250                 255
```

-continued

```
Tyr Gln Phe Arg Tyr Gln Asn Arg Val Ser Asn Cys Gln Ile Glu Ala
            260                 265                 270

Trp Ile Asn Tyr Lys Asp Leu Ile Ser Leu Pro Ala Glu Gly Gln Trp
        275                 280                 285

Ser Lys Met Ala Pro Ser Arg Ile Met Ser Phe Asp Ile Glu Cys Ala
    290                 295                 300

Gly Arg Lys Gly Val Phe Pro Asp Pro Ser Ile Asp Pro Val Ile Gln
305                 310                 315                 320

Ile Ala Ser Ile Val Thr Gln Tyr Gly Asp Ser Thr Pro Phe Val Arg
                325                 330                 335

Asn Val Phe Cys Val Asp Thr Cys Ser Gln Ile Val Gly Thr Gln Val
            340                 345                 350

Tyr Glu Phe Gln Asn Gln Ala Glu Met Leu Ser Ser Trp Ser Lys Phe
        355                 360                 365

Val Arg Asp Val Asp Pro Asp Val Leu Ile Gly Tyr Asn Ile Cys Asn
    370                 375                 380

Phe Asp Ile Pro Tyr Leu Leu Asp Arg Ala Lys Ser Leu Arg Ile His
385                 390                 395                 400

Asn Phe Pro Leu Leu Gly Arg Ile His Asn Phe Phe Ser Val Ala Lys
            405                 410                 415

Glu Thr Thr Phe Ser Ser Lys Ala Tyr Gly Thr Arg Glu Ser Lys Thr
        420                 425                 430

Thr Ser Ile Pro Gly Arg Leu Gln Leu Asp Met Leu Gln Val Met Gln
    435                 440                 445

Arg Asp Phe Lys Leu Arg Ser Tyr Ser Leu Asn Ala Val Cys Ser Gln
450                 455                 460

Phe Leu Gly Glu Gln Lys Glu Asp Val His Tyr Ser Ile Ile Thr Asp
465                 470                 475                 480

Leu Gln Asn Gly Thr Ala Asp Ser Arg Arg Arg Leu Ala Ile Tyr Cys
                485                 490                 495

Ser Lys Asp Ala Tyr Leu Pro Gln Arg Leu Met Asp Lys Leu Met Cys
            500                 505                 510

Phe Val Asn Tyr Thr Glu Met Ala Arg Val Thr Gly Val Pro Phe Asn
        515                 520                 525

Phe Leu Leu Ala Arg Gly Gln Gln Ile Lys Val Ile Ser Gln Leu Phe
    530                 535                 540

Arg Lys Ala Leu Gln His Asp Leu Val Val Pro Asn Ile Arg Val Asn
545                 550                 555                 560

Gly Thr Asp Glu Gln Tyr Glu Gly Ala Thr Val Ile Glu Pro Ile Lys
                565                 570                 575

Gly Tyr Tyr Asp Thr Pro Ile Ala Thr Ser Asp Phe Ser Ser Leu Tyr
            580                 585                 590

Pro Ser Ile Met Gln Ala His Asn Leu Cys Tyr Thr Thr Leu Leu Asp
        595                 600                 605

Ser Asn Thr Ala Glu Leu Leu Lys Leu Lys Gln Asp Val Asp Tyr Ser
    610                 615                 620

Val Thr Pro Asn Gly Asp Tyr Phe Val Lys Pro His Val Arg Lys Gly
625                 630                 635                 640

Leu Leu Pro Ile Ile Leu Ala Asp Leu Asn Ala Arg Lys Lys Ala
                645                 650                 655

Lys Ala Asp Leu Lys Lys Glu Thr Asp Pro Phe Lys Lys Ala Val Leu
            660                 665                 670
```

```
Asp Gly Arg Gln Leu Ala Leu Lys Val Ser Ala Asn Ser Val Tyr Gly
        675                 680                 685

Phe Thr Gly Ala Thr Asn Gly Arg Leu Pro Cys Leu Ala Ile Ser Ser
        690                 695                 700

Ser Val Thr Ser Tyr Gly Arg Gln Met Ile Glu Lys Thr Lys Asp Val
705                 710                 715                 720

Val Glu Lys Arg Tyr Arg Ile Glu Asn Gly Tyr Ser His Asp Ala Val
                725                 730                 735

Val Ile Tyr Gly Asp Thr Asp Ser Val Met Val Lys Phe Gly Val Lys
            740                 745                 750

Thr Leu Pro Glu Ala Met Lys Leu Gly Glu Glu Ala Ala Asn Tyr Val
        755                 760                 765

Ser Asp Gln Phe Pro Asn Pro Ile Lys Ser Glu Phe Glu Lys Val Tyr
        770                 775                 780

Phe Pro Tyr Leu Leu Ile Ser Lys Lys Arg Tyr Ala Gly Leu Phe Trp
785                 790                 795                 800

Thr Arg Thr Asp Thr Tyr Asp Lys Met Asp Ser Lys Gly Ile Glu Thr
                805                 810                 815

Val Arg Arg Asp Asn Cys Pro Leu Val Ser Tyr Val Ile Asp Thr Ala
            820                 825                 830

Leu Arg Lys Met Leu Ile Asp Gln Asp Val Glu Gly Ala Gln Leu Phe
        835                 840                 845

Thr Lys Lys Val Ile Ser Asp Leu Leu Gln Asn Lys Ile Asp Met Ser
850                 855                 860

Gln Leu Val Ile Thr Lys Ala Leu Ser Lys Thr Asp Tyr Ala Ala Lys
865                 870                 875                 880

Met Ala His Val Glu Leu Ala Glu Arg Met Arg Lys Arg Asp Ala Gly
            885                 890                 895

Ser Ala Pro Ala Ile Gly Asp Arg Val Ala Tyr Val Ile Ile Lys Gly
        900                 905                 910

Ala Gln Gly Asp Gln Phe Tyr Met Arg Ser Glu Asp Pro Ile Tyr Val
        915                 920                 925

Leu Glu Asn Asn Ile Pro Ile Asp Ala Lys Tyr Tyr Leu Glu Asn Gln
        930                 935                 940

Leu Ser Lys Pro Leu Leu Arg Ile Phe Glu Pro Ile Leu Gly Glu Lys
945                 950                 955                 960

Ala Ser Ser Leu Leu His Gly Asp His Thr Arg Thr Ile Ser Met Ala
                965                 970                 975

Ala Pro Ser Val Gly Gly Ile Met Lys Phe Ala Val Lys Val Glu Thr
            980                 985                 990

Cys Leu Gly Cys Lys Ala Pro Ile Lys Lys Gly Lys Thr Ala Leu Cys
        995                 1000                1005

Glu Asn Cys Leu Asn Arg Ser Ala Glu Ser Tyr Gln Arg Gln Val
        1010                1015                1020

Ala Gln Val Asn Asp Leu Glu Val Arg Phe Ala Arg Leu Trp Thr
        1025                1030                1035

Gln Cys Gln Arg Cys Gln Gly Ser Met His Gln Asp Val Ile Cys
        1040                1045                1050

Thr Ser Arg Asp Cys Pro Ile Phe Tyr Met Arg Ile Ala Glu His
        1055                1060                1065
```

```
Lys Lys Leu Gln Gln Ser Val Asp Leu Ser Lys Arg Phe Asp Glu
        1070                1075                1080

Met Ser Trp
    1085

<210> SEQ ID NO 8
<211> LENGTH: 3261
<212> TYPE: DNA
<213> ORGANISM: Schizosaccharomyces pombe

<400> SEQUENCE: 8
atgacagata ggtcttcaaa tgagggcgtc gtgttaaata agaaaaacta tccatttccc      60
cgaagaaatg gttcaattca tggcgaaatt acagatgtca acggcgacg  tttaagcgaa     120 agaaatggat atggtgataa aaagggctca tcctcaaaag aaaaaacttc atcttttgag     180
gatgagctgg ctgaatacgc ttcacaattg gaccaagatg aaataaaatc ttcaaaagat     240
cagcagtggc aacgaccagc tttacctgca ataaatcctg agaaggatga tatttatttt     300
cagcaaatcg atagtgagga gttcacagaa ggatctgtac cttcaattcg tttgtttggt     360
gttactgaca tggaaacag  catccttgtt catgttgtgg gattccttcc gtacttttat     420
gttaaagccc cggttggatt tcgacctgag atgctagaac gtttcacaca agatttagat     480
gctacttgta tgggggtgt  gatcgatcat tgcattatag atgaaggaa aatttatat      540 ggatttcagg gaaatgaaaa atctccattc attaaaatct ttactactaa ccctcgtata     600
ttatctcgag cacgaaatgt atttgaaaga ggagaattca acttcgaaga gcttttccct     660
gttggtgtcg gtgtcactac ttttgagagc aatacgcaat atcttcttag attcatgatt     720
gactgtgatg ttgttggtat gaattggatt catcttcctg cttcaaaata tcaatttcgt     780
taccagaatc gagtttctaa ttgtcaaatt gaagcttgga ttaattacaa agacttgatc     840
agtcttccag ctgaaggcca gtggtctaaa atggccccac tgaggatcat gagctttgat     900
attgaatgcg caggtcgcaa aggcgttttt cctgatccct ctattgaccc tgtaattcaa     960
attgcaagta tagtaacgca gtatggagac tccactcctt tgttcgtaa  tgtcttttgt    1020 gttgatacat gctcacaaat cgttggaaca caagtatatg aatttcaaaa tcaggctgaa    1080
atgctttcaa gttggtcaaa attgttcgt  gatgttgacc cagatgtttt aattgggtac    1140
aacatctgca actttgatat cccttacctc ttggatcgag caaaaagctt acgcattcac    1200
aatttcccat tacttggccg tattcataat tttttttctg tcgcaaagga aaccacgttt    1260
tcaagtaaag catatggtac tcgtgaaagc aaaaccacta gtattcctgg gcgtttgcag    1320
cttgatatgt tacaagtaat gcagcgtgat tttaagcttc gatcttactc tttaaatgca    1380
gtctgctctc agtttctagg cgagcaaaaa gaagatgtac actattctat catcactgac    1440
ttgcaaaatg gcactgccga ttctagaaga cgtttagcta tttattgtct gaaagatgca    1500
tatttacccc aacgcttaat ggacaaatta atgtgttttg ttaactatac tgaaatggca    1560
agagtaacag gtgtaccgtt taattttctt cttgctagag ccaacagat  aaagttatt     1620 tctcaattgt ttcgcaaagc tcttcaacat gacctagttg ttccaaatat acgtgtaaat    1680
ggaacagatg agcaatatga aggtgctaca gtcattgaac cgattaaagg atactatgat    1740 accctattg  caacactgga ttttagttca ctttatcctt cgattatgca agcccataat    1800
ttatgctata cgacattact tgactcaaat actgcagaat tattaaaact taagcaagat    1860
gttgactact cagtgactcc gaacggagat tatttcgtta aaccacatgt tcgtaaagga    1920
ctactcccta ttatcttagc tgatttactt aatgcacgta agaaagcaaa agcagatcta    1980
```

```
aaaaaggaaa cggacccatt caaaaaggct gttttggatg gtagacagct agctttaaaa   2040
gtaagtgcta attcagtata tggatttact ggtgctacca acggacgttt gccgtgttta   2100
gcaatttctt cttctgttac ctcttatggt cgacaaatga ttgaaaaaac caaggatgtt   2160
gtagaaaaga gatacagaat tgagaatgga tactctcacg atgcagttgt aatctatggt   2220
gacactgatt ctgttatggt taagtttggc gttaaaacgt tacctgaagc catgaaatta   2280
ggagaggaag cagctaatta tgtttcagac cagtttccga atcctattaa actggagttt   2340
gagaaagtgt actttccata tcttttaatt tccaaaaaac gttatgcagg attattttgg   2400
actcgtacag atacttatga taaatggac tctaaaggaa tagaaactgt cagaagagat   2460
aactgtcctc tagtatctta tgtgattgac acagctttga gaaaaatgtt aattgatcag   2520
gatgtagagg gtgcacagtt gtttacaaaa aaagttattt ccgatttgtt acaaaacaaa   2580
attgatatgt cacaacttgt aatcacaaag gcattatcaa aaactgatta tgctgccaaa   2640
atggcacacg ttgaattggc tgagcgaatg cgtaaacgag atgctggctc cgccccagcc   2700
ataggagatc gcgttgcata cgttattatt aaaggtgcac aaggtgatca atttttatatg   2760 aggtcggagg accctatata tgtattggaa ataacattc ctattgatgc aaaatattat   2820
ttggaaaatc aactctccaa acctttgctt agaattttttg agcctattct tggtgaaaaa   2880
gctagctctt tacttcatgg tgaccatact cggacgattt ccatggcagc ccccagtgtt   2940
ggaggaataa tgaaattcgc agtaaaggtt gagacctgtc ttggatgcaa agctcccata   3000 aaaaaggta aaactgcttt atgtgagaat tgtctaaata gatcggcgga actgtatcaa   3060
cgtcaggttg ctcaagtgaa tgatttagaa gttcgttttg ctcgcttatg gactcaatgt   3120
cagcgatgcc aaggaagtat gcatcaagac gtcatttgta ccagtagaga ctgccccata   3180
ttttatatgc gaattgcaga acacaagaaa cttcagcaat ctgttgactt actgaaaaga   3240
tttgatgaaa tgtcctggtg a                                            3261
```

<210> SEQ ID NO 9
<211> LENGTH: 1086
<212> TYPE: PRT
<213> ORGANISM: Schizosaccharomyces pombe
<400> SEQUENCE: 9

```
Met Thr Asp Arg Ser Ser Asn Glu Gly Val Val Leu Asn Lys Glu Asn
1               5                   10                  15

Tyr Pro Phe Pro Arg Arg Asn Gly Ser Ile His Gly Glu Ile Thr Asp
            20                  25                  30

Val Lys Arg Arg Arg Leu Ser Glu Arg Asn Gly Tyr Gly Asp Lys Lys
        35                  40                  45

Gly Ser Ser Ser Lys Glu Lys Thr Ser Ser Phe Glu Asp Glu Ser Ala
    50                  55                  60

Glu Tyr Ala Ser Gln Leu Asp Gln Asp Glu Ile Lys Ser Ser Lys Asp
65                  70                  75                  80

Gln Gln Trp Gln Arg Pro Ala Leu Pro Ala Ile Asn Pro Glu Lys Asp
                85                  90                  95

Asp Ile Tyr Phe Gln Gln Ile Asp Ser Glu Glu Phe Thr Glu Gly Ser
            100                 105                 110

Val Pro Ser Ile Arg Leu Phe Gly Val Thr Asp Asn Gly Asn Ser Ile
        115                 120                 125

Leu Val His Val Val Gly Phe Leu Pro Tyr Phe Tyr Val Lys Ala Pro
    130                 135                 140
```

-continued

```
Val Gly Phe Arg Pro Glu Met Leu Glu Arg Phe Thr Gln Asp Leu Asp
145                 150                 155                 160

Ala Thr Cys Asn Gly Val Ile Asp His Cys Ile Ile Glu Met Lys
            165                 170                 175

Glu Asn Leu Tyr Gly Phe Gln Gly Asn Glu Lys Ser Pro Phe Ile Lys
            180                 185                 190

Ile Phe Thr Thr Asn Pro Arg Ile Leu Ser Arg Ala Arg Asn Val Phe
        195                 200                 205

Glu Arg Gly Glu Phe Asn Phe Glu Glu Leu Phe Pro Val Gly Val Gly
        210                 215                 220

Val Thr Thr Phe Glu Ser Asn Thr Gln Tyr Leu Leu Arg Phe Met Ile
225                 230                 235                 240

Asp Cys Asp Val Val Gly Met Asn Trp Ile His Leu Pro Ala Ser Lys
                245                 250                 255

Tyr Gln Phe Arg Tyr Gln Asn Arg Val Ser Asn Cys Gln Ile Glu Ala
                260                 265                 270

Trp Ile Asn Tyr Lys Asp Leu Ile Ser Leu Pro Ala Glu Gly Gln Trp
            275                 280                 285

Ser Lys Met Ala Pro Ser Arg Ile Met Ser Phe Ala Gly Ala Cys Ala
290                 295                 300

Gly Arg Lys Gly Val Phe Pro Asp Pro Ser Ile Asp Pro Val Ile Gln
305                 310                 315                 320

Ile Ala Ser Ile Val Thr Gln Tyr Gly Asp Ser Thr Pro Phe Val Arg
                325                 330                 335

Asn Val Phe Cys Val Asp Thr Cys Ser Gln Ile Val Gly Thr Gln Val
            340                 345                 350

Tyr Glu Phe Gln Asn Gln Ala Glu Met Leu Ser Ser Trp Ser Lys Phe
            355                 360                 365

Val Arg Asp Val Asp Pro Asp Val Leu Ile Gly Tyr Asn Ile Cys Asn
370                 375                 380

Phe Asp Ile Pro Tyr Leu Leu Asp Arg Ala Lys Ser Leu Arg Ile His
385                 390                 395                 400

Asn Phe Pro Leu Leu Gly Arg Ile His Asn Phe Phe Ser Val Ala Lys
                405                 410                 415

Glu Thr Thr Phe Ser Ser Lys Ala Tyr Gly Thr Arg Glu Ser Lys Thr
                420                 425                 430

Thr Ser Ile Pro Gly Arg Leu Gln Leu Asp Met Leu Gln Val Met Gln
            435                 440                 445

Arg Asp Phe Lys Leu Arg Ser Tyr Ser Leu Asn Ala Val Cys Ser Gln
        450                 455                 460

Phe Leu Gly Glu Gln Lys Glu Asp Val His Tyr Ser Ile Ile Thr Asp
465                 470                 475                 480

Leu Gln Asn Gly Thr Ala Asp Ser Arg Arg Leu Ala Ile Tyr Cys
            485                 490                 495

Ser Lys Asp Ala Tyr Leu Pro Gln Arg Leu Met Asp Lys Leu Met Cys
                500                 505                 510

Phe Val Asn Tyr Thr Glu Met Ala Arg Val Thr Gly Val Pro Phe Asn
            515                 520                 525

Phe Leu Leu Ala Arg Gly Gln Gln Ile Lys Val Ile Ser Gln Leu Phe
        530                 535                 540

Arg Lys Ala Leu Gln His Asp Leu Val Val Pro Asn Ile Arg Val Asn
545                 550                 555                 560
```

-continued

```
Gly Thr Asp Glu Gln Tyr Gly Ala Thr Val Ile Glu Pro Ile Lys
                565                 570                 575

Gly Tyr Tyr Asp Thr Pro Ile Ala Thr Ser Asp Phe Ser Ser Leu Tyr
                580                 585                 590

Pro Ser Ile Met Gln Ala His Asn Leu Cys Tyr Thr Thr Leu Leu Asp
                595                 600                 605

Ser Asn Thr Ala Glu Leu Leu Lys Leu Lys Gln Asp Val Asp Tyr Ser
            610                 615                 620

Val Thr Pro Asn Gly Asp Tyr Phe Val Lys Pro His Val Arg Lys Gly
625                 630                 635                 640

Leu Leu Pro Ile Ile Leu Ala Asp Leu Leu Asn Ala Arg Lys Lys Ala
                645                 650                 655

Lys Ala Asp Leu Lys Lys Glu Thr Asp Pro Phe Lys Lys Ala Val Leu
            660                 665                 670

Asp Gly Arg Gln Leu Ala Leu Lys Val Ser Ala Asn Ser Val Tyr Gly
            675                 680                 685

Phe Thr Gly Ala Thr Asn Gly Arg Leu Pro Cys Leu Ala Ile Ser Ser
    690                 695                 700

Ser Val Thr Ser Tyr Gly Arg Gln Met Ile Glu Lys Thr Lys Asp Val
705                 710                 715                 720

Val Glu Lys Arg Tyr Arg Ile Glu Asn Gly Tyr Ser His Asp Ala Val
                725                 730                 735

Val Ile Tyr Gly Asp Thr Asp Ser Val Met Val Lys Phe Gly Val Lys
                740                 745                 750

Thr Leu Pro Glu Ala Met Lys Leu Gly Glu Glu Ala Ala Asn Tyr Val
            755                 760                 765

Ser Asp Gln Phe Pro Asn Pro Ile Lys Ser Glu Phe Glu Lys Val Tyr
            770                 775                 780

Phe Pro Tyr Leu Leu Ile Ser Lys Lys Arg Tyr Ala Gly Leu Phe Trp
785                 790                 795                 800

Thr Arg Thr Asp Thr Tyr Asp Lys Met Asp Ser Lys Gly Ile Glu Thr
                805                 810                 815

Val Arg Arg Asp Asn Cys Pro Leu Val Ser Tyr Val Ile Asp Thr Ala
                820                 825                 830

Leu Arg Lys Met Leu Ile Asp Gln Asp Val Glu Gly Ala Gln Leu Phe
                835                 840                 845

Thr Lys Lys Val Ile Ser Asp Leu Leu Gln Asn Lys Ile Asp Met Ser
            850                 855                 860

Gln Leu Val Ile Thr Lys Ala Leu Ser Lys Thr Asp Tyr Ala Ala Lys
865                 870                 875                 880

Met Ala His Val Glu Leu Ala Glu Arg Met Arg Lys Arg Asp Ala Gly
                885                 890                 895

Ser Ala Pro Ala Ile Gly Asp Arg Val Ala Tyr Val Ile Ile Lys Gly
            900                 905                 910

Ala Gln Gly Asp Gln Phe Tyr Met Arg Ser Glu Asp Pro Ile Tyr Val
    915                 920                 925

Leu Glu Asn Asn Ile Pro Ile Asp Ala Lys Tyr Tyr Leu Glu Asn Gln
    930                 935                 940

Leu Ser Lys Pro Leu Leu Arg Ile Phe Glu Pro Ile Leu Gly Glu Lys
945                 950                 955                 960

Ala Ser Ser Leu Leu His Gly Asp His Thr Arg Thr Ile Ser Met Ala
                965                 970                 975
```

```
Ala Pro Ser Val Gly Gly Ile Met Lys Phe Ala Val Lys Val Glu Thr
            980                 985                 990

Cys Leu Gly Cys Lys Ala Pro Ile Lys Lys Gly Lys Thr  Ala Leu Cys
            995                1000                1005

Glu Asn  Cys Leu Asn Arg Ser  Ala Glu Ser Tyr Gln  Arg Gln Val
    1010                1015                1020

Ala Gln  Val Asn Asp Leu Glu  Val Arg Phe Ala Arg  Leu Trp Thr
    1025                1030                1035

Gln Cys  Gln Arg Cys Gln Gly  Ser Met His Gln Asp  Val Ile Cys
    1040                1045                1050

Thr Ser  Arg Asp Cys Pro Ile  Phe Tyr Met Arg Ile  Ala Glu His
    1055                1060                1065

Lys Lys  Leu Gln Gln Ser Val  Asp Leu Ser Lys Arg  Phe Asp Glu
    1070                1075                1080

Met Ser  Trp
    1085

<210> SEQ ID NO 10
<211> LENGTH: 3261
<212> TYPE: DNA
<213> ORGANISM: Schizosaccharomyces pombe

<400> SEQUENCE: 10
atgacagata ggtcttcaaa tgagggcgtc gtgttaaata agaaaacta tccatttccc      60 cgaagaaatg gttcaattca tggcgaaatt acagatgtca acggcgacg  tttaagcgaa    120 agaaatggat atggtgataa aaagggctca tcctcaaaag aaaaaacttc atcttttgag    180
gatgagctgg ctgaatacgc ttcacaattg gaccaagatg aaataaaatc ttcaaaagat    240
cagcagtggc aacgaccagc tttacctgca ataaatcctg agaaggatga tatttatttt    300
cagcaaatcg atagtgagga gttcacagaa ggatctgtac cttcaattcg tttgtttggt    360
gttactgaca atggaaacag catccttgtt catgttgtgg gattccttcc gtactttat    420 gttaaagccc cggttggatt tcgacctgag atgctagaac gtttcacaca agatttagat    480
gctacttgta atggggtgt gatcgatcat tgcattatag agatgaagga aaatttatat    540
ggatttcagg gaaatgaaaa atctccattc attaaaatct ttactactaa ccctcgtata    600
ttatctcgag cacgaaatgt atttgaaaga ggagaattca acttcgaaga gcttttccct    660
gttggtgtcg gtgtcactac ttttgagagc aatacgcaat atcttcttag attcatgatt    720
gactgtgatg ttgttggtat gaattggatt catcttcctg cttcaaaata tcaatttcgt    780
taccagaatc gagtttctaa ttgtcaaatt gaagcttgga ttaattacaa agacttgatc    840
agtcttccag ctgaaggcca gtggtctaaa atggccccac tgaggatcat gagctttgcc    900
ggcgcttgcg caggtcgcaa aggcgttttt cctgatccct ctattgaccc tgtaattcaa    960
attgcaagta tagtaacgca gtatggagac tccactcctt tgttcgtaa tgtcttttgt   1020 gttgatacat gctcacaaat cgttggaaca caagtatatg aatttcaaaa tcaggctgaa   1080
atgctttcaa gttggtcaaa atttgttcgt gatgttgacc cagatgtttt aattgggtac   1140
aacatctgca actttgatat cccttacctc ttggatcgag caaaaagctt acgcattcac   1200
aatttcccat tacttggccg tattcataat tttttttctg tcgcaaagga aaccacgttt   1260
tcaagtaaag catatggtac tcgtgaaagc aaaaccacta gtattcctgg gcgtttgcag   1320
cttgatatgt tacaagtaat gcagcgtgat tttaagcttc gatcttactc tttaaatgca   1380
gtctgctctc agtttctagg cgagcaaaaa gaagatgtac actattctat catcactgac   1440
```

-continued

```
ttgcaaaatg gcactgccga ttctagaaga cgtttagcta tttattgtct gaaagatgca    1500
tatttacccc aacgcttaat ggacaaatta atgtgttttg ttaactatac tgaaatggca    1560
agagtaacag gtgtaccgtt taattttctt cttgctagag gccaacagat taaagttatt    1620
tctcaattgt ttcgcaaagc tcttcaacat gacctagttg ttccaaatat acgtgtaaat    1680
ggaacagatg agcaatatga aggtgctaca gtcattgaac cgattaaagg atactatgat    1740 accccctattg caacactgga ttttagttca ctttatcctt cgattatgca agcccataat    1800
ttatgctata cgacattact tgactcaaat actgcagaat tattaaaact taagcaagat    1860
gttgactact cagtgactcc gaacggagat tatttcgtta aaccacatgt tcgtaaagga    1920
ctactcccta ttatcttagc tgatttactt aatgcacgta agaaagcaaa agcagatcta    1980
aaaaaggaaa cggacccatt caaaaaggct gttttggatg gtagacagct agctttaaaa    2040
gtaagtgcta attcagtata tggatttact ggtgctacca acggacgttt gccgtgttta    2100
gcaatttctt cttctgttac ctcttatggt cgacaaatga ttgaaaaaac caaggatgtt    2160
gtagaaaaga gatacagaat tgagaatgga tactctcacg atgcagttgt aatctatggt    2220
gacactgatt ctgttatggt taagtttggc gttaaaacgt tacctgaagc catgaaatta    2280
ggagaggaag cagctaatta tgtttcagac cagtttccga atcctattaa actggagttt    2340
gagaaagtgt actttccata tcttttaatt tccaaaaaac gttatgcagg attattttgg    2400
actcgtacag atacttatga taaaatggac tctaaaggaa tagaaactgt cagaagagat    2460
aactgtcctc tagtatctta tgtgattgac acagctttga gaaaaatgtt aattgatcag    2520
gatgtagagg gtgcacagtt gtttacaaaa aaagttattt ccgatttgtt acaaaacaaa    2580
attgatatgt cacaacttgt aatcacaaag gcattatcaa aaactgatta tgctgccaaa    2640
atggcacacg ttgaattggc tgagcgaatg cgtaaacgag atgctggctc cgccccagcc    2700
ataggagatc gcgttgcata cgttattatt aaaggtgcac aaggtgatca attttatatg    2760
aggtcggagg accctatata tgtattggaa ataacattc ctattgatgc aaaatattat    2820
ttggaaaatc aactctccaa accttttgctt agaattttg agcctattct tggtgaaaaa    2880
gctagctctt tacttcatgg tgaccatact cggacgattt ccatggcagc ccccagtgtt    2940
ggaggaataa tgaaattcgc agtaaaggtt gagacctgtc ttggatgcaa agctcccata    3000
aaaaaaggta aaactgcttt atgtgagaat tgtctaaata gatcggcgga actgtatcaa    3060
cgtcaggttg ctcaagtgaa tgatttagaa gttcgttttg ctcgcttatg gactcaatgt    3120
cagcgatgcc aaggaagtat gcatcaagac gtcatttgta ccagtagaga ctgccccata    3180
ttttatatgc gaattgcaga acacaagaaa cttcagcaat ctgttgactt actgaaaaga    3240
tttgatgaaa tgtcctggtg a                                              3261
```

```
<210> SEQ ID NO 11
<211> LENGTH: 42
<212> TYPE: DNA
<213> ORGANISM: artificial sequence
<220> FEATURE:
<223> OTHER INFORMATION: primer

<400> SEQUENCE: 11
agctcggatc cgatgacaga taggtcttca aatgagggcg tc                        42

<210> SEQ ID NO 12
<211> LENGTH: 38
<212> TYPE: DNA
<213> ORGANISM: artificial sequence
```

-continued

```
<220> FEATURE:
<223> OTHER INFORMATION: primer

<400> SEQUENCE: 12
tcgaggcgac ctgcgcaagc gccggcaaag ctcatgat                          38

<210> SEQ ID NO 13
<211> LENGTH: 42
<212> TYPE: DNA
<213> ORGANISM: artificial sequence
<220> FEATURE:
<223> OTHER INFORMATION: primer

<400> SEQUENCE: 13
agctcaggat catgagcttt gccggcgctt gcgcaggtcg ca                     42

<210> SEQ ID NO 14
<211> LENGTH: 42
<212> TYPE: DNA
<213> ORGANISM: artificial sequence
<220> FEATURE:
<223> OTHER INFORMATION: primer

<400> SEQUENCE: 14
tcgaggcggc cgctcaccag gacatttcat caaatctttt ca                     42
```

The invention claimed is:

1. A yeast deposited at the National Institute of Advanced Industrial Science and Technology Patent Organism Depositary in Japan having an accession number of "FERM BP-11122."

2. A yeast deposited at the National Institute of Advanced Industrial Science and Technology Patent Organism Depositary in Japan having an accession number of "FERM BP-11123."

3. A yeast deposited at the National Institute of Advanced Industrial Science and Technology Patent Organism Depositary in Japan having an accession number of "FERM BP-11124."

* * * * *